US006781030B1

(12) United States Patent
Baguisi et al.

(10) Patent No.: US 6,781,030 B1
(45) Date of Patent: Aug. 24, 2004

(54) METHODS FOR CLONING MAMMALS USING TELOPHASE OOCYTES

(75) Inventors: Alexander Baguisi, Grafton, MA (US); Eric W. Overstrom, Grafton, MA (US)

(73) Assignee: Trustee of Tufts College, Ballou Hall, Medford, MA (US)

( * ) Notice: Subject to any disclaimer, the term of this patent is extended or adjusted under 35 U.S.C. 154(b) by 17 days.

(21) Appl. No.: 09/432,906

(22) Filed: Nov. 2, 1999

Related U.S. Application Data
(60) Provisional application No. 60/149,317, filed on Aug. 17, 1999, provisional application No. 60/131,061, filed on Apr. 26, 1999, provisional application No. 60/131,328, filed on Apr. 26, 1999, and provisional application No. 60/106,728, filed on Nov. 2, 1998.

(51) Int. Cl.[7] ............................................. C12N 15/00
(52) U.S. Cl. .............................. 800/24; 800/8; 800/14; 435/377
(58) Field of Search ............................... 800/8, 14, 24; 435/377

(56) References Cited

U.S. PATENT DOCUMENTS

| | | | |
|---|---|---|---|
| 5,496,720 A | 3/1996 | Susko-Parrish et al. | 435/240.2 |
| 5,843,705 A | 12/1998 | DiTullio et al. | 435/69.1 |
| 5,843,754 A | 12/1998 | Susko-Parrish et al. | 435/240 |
| 5,905,042 A | 5/1999 | Stice et al. | 435/373 |
| 5,945,577 A | 8/1999 | Stice et al. | 800/24 |
| 5,952,222 A | 9/1999 | Rosenkrans, Jr. et al. | 435/325 |
| 5,994,619 A | 11/1999 | Stice et al. | 800/21 |
| 6,147,276 A | 11/2000 | Campbell et al. | 800/24 |
| 6,252,133 B1 | 6/2001 | Campbell et al. | 800/24 |
| 2002/0035737 A1 | 3/2002 | Stice et al. | |

FOREIGN PATENT DOCUMENTS

| | | |
|---|---|---|
| GB | 2318578 A | 4/1998 |
| GB | 2331751 A | 6/1999 |
| WO | WO 95/03398 | 2/1995 |
| WO | WO 96/26268 | 8/1996 |
| WO | WO-07668 * | 3/1997 |
| WO | WO 98/29532 | 9/1998 |
| WO | WO 99/01163 | 1/1999 |
| WO | WO 99/01164 | 1/1999 |
| WO | WO 99/37143 | 7/1999 |
| WO | WO 00/26357 | 11/2000 |

OTHER PUBLICATIONS

S. Meinecke–Tillman, Nature,"Experimental chimaeras—removal of reproductive barrier between sheep and goat," Feb. 1984, vol. 307, pp. 637–638.*
V. Bordignon et al., Molecular Reproduction and Development, "Telophase Enucleation: An improved method to prepare recipient cytoplasts for use in bovine nuclear transfer," (1998), 49:29–36.*
B. Wu et al., Biology of Reproduction, "Dynamics of maturation–promoting factor and its constituent proteins during in vitro maturation of bovine oocytes," (1997), 56, pp. 253–259.*
K.M. Ebert et al., Bio/Technology, "Transgenic production of a variant of human tissue–type plasminogen activator in goat milk:Generation of transgenic goats and analysis of expression," Sep. 1991, vol. 9, pp. 835–838.*
Liu, L., et al., "Nuclear remodelling and early development in cryopreserved, porcine primordial germ cells following nuclear transfer into in vitro–matured oocytes," Int. J. Dev. Biol. 39:639–644 (1995).
Presicce, G.A. and Yang, X., "Parthenogenetic Development of Bovine Oocytes Matured In Vitro for 24 Hr and Activated by Ethanol and Cycloheximide," Molecular Reproduction and Development 38:380–385 (1994).
Schnieke, A.E., et al., "Human Factor IX Transgenic Sheep Procuded by Transfer of Nuclei from Transfected Fetal Fibroblasts," Science 278:2130–2133 (1997).
Vignon, X., et al., "Developmental potential of bovine embryos reconstructed from enucleated matured oocytes fused with cultured somatic cells," Life Sciences 321:735–745 (1998).
Wakayama, T., et al., "Full–term development of mice from enucleated oocytes injected with cumulus cell nuclei," Nature 394:369–374 (1998).
Tanaka, H., et al., "Influence of Time After the Removal of Nocodazole from Nuclear Donors on the Development of Reconstituted Embryos in Bovine Nuclear Transplantation," Jpn. J. Vet. Res., 43(3–4):135–143 (1995).
Prather, R.S., et al., "Cloning Embryos by Nuclear Transfer," J. Reprod. Fert., Suppl., 41:125–134 (1990).
Campbell, K.H.S., et al., "Cell Cycle Co–ordination in Embryo Cloning by Nuclear Transfer," Reviews of Reproduction, 1:40–46 (1996).
Gorgidze, L.A., et al., "Centrosome and Microtubules Behaviour in the Cytoplasts," J. Submicrosc. Cytol. Pathol., 27(3):381–389 (1995).
Liu, L., et al., "Nuclear Transfer in Sheep Embryos: The Effect of Cell–Cycle Coordination Between Nucleus and Cytoplasm and the Use of In Vitro Matured Oocytes," Molecular Reproduction and Development, 47:255–264 (1997).
Kanka, J., et al., "Nucleolar Ultrastructure in Bovine Nuclear Transfer Embryos," Molecular Reproduction and Development, 52(3):253–263 (1999).

(List continued on next page.)

Primary Examiner—Deborah Crouch
(74) Attorney, Agent, or Firm—Ingrid A. Beattie; Mintz, Levin, Cohn, Ferris, Glovsky and Popeo P.C.

(57) ABSTRACT

The present invention pertains to methods for cloning animals. In particular, the invention includes methods of cloning an animal by combining a genome from an activated donor cell with an activated enucleated oocyte to thereby obtain a nuclear transfer embryo, and impregnating an animal with the nuclear transfer embryo in conditions suitable for gestation of a cloned animal. The invention further relates to methods of chemically enucleating an oocyte having a meiotic spindle apparatus by exposing the oocyte with a compound that destabilizes the meiotic spindle apparatus.

60 Claims, No Drawings

OTHER PUBLICATIONS

Kono, T., "Nuclear Transfer and Reprogramming," *Reviews of Reproduction*, 2(2):74–80 (1997).

Pinto–Correia, C., et al., "Embryo Development: Factors Involved in Nuclear Reprogramming During Early Development in the Rabbit," *Molecular Reproduction and Development*, 40(3):292–304 (1995).

Campbell, K.H.S., et al., "Nuclear–Cytoplasmic Interactions During the First Cell Cycle of Nuclear Transfer Reconstructed Bovine Embryos: Implications for Deoxyribonucleic Acid Replication and Development," *Biology of Reproduction*, 49(5):933–942 (1993).

Collas, P., et al., "Influence Cell Cycle Stage of the Donor Nucleus on Development of Nuclear Transplant Rabbit Embryos," *Biology of Reproduction*, 46(3):492–500 (1992).

Kanka, J., "Nuclear Transplantation: Reprogramming of Transplanted nuclei," *Reprod. Nutr. Dev.*, 39(5–6):545–554 (1999).

Collas, P., et al., "Effect of Donor Cell Cycle Stage on Chromatin and Spindle Morphology in Nuclear Transplant Rabbit Embryos," *Biology of Reproduction*, 46(3):501–511 (1992).

Wakayama, T., et al., "Mice Cloned from Embryonic Stem Cells," *PNAS*, 96(26):14984–14989 (1999).

Kubota, C., et al., "Six Cloned Calves Produced from Adult Fibroblast Cells After Long–term Culture," *Proc. Natl. Acad. Sci. USA*, 97(3):990–995 (2000).

Baguisi, A., et al., "Production of goats by somatic cell nuclear transfer," *Nature Biotechnology*, 17:456–461 (1999).

Yong, Z., et al., "Nuclear–Cytoplasmic Interaction and Development of Goat Embryos Reconstructed by Nuclear Transplantation: Production of Goats by Serially Cloning Embryos", *Biology of Reproduction*, 58:266–269 (1998).

Cibelli, J.B., et al., "Cloned Transgenic Calves Produced from Nonquiescent Fetal Fibroblasts", *Science*, 280:1256–1258 (1998).

Campbell, K.H.S., et al., "Sheep cloned by nuclear transfer from a cultured cell line", *Nature*, 380:64–66 (1996).

Campbell, K.H.S., et al., "Featured Article: Cloning Farm Animals by Nuclear Transfer: From Cell Cycles to Cells", *Embryo Transfer Newsletter*, 14(1):12–16 (1996).

Bordignon, V. and Smith, L.C., "Telophase enucleation: an improved method to prepare recipient cytoplasts for use in bovine nuclear transfer," *Molecular Reproduction and Development*, 49:29–36 (1998).

Wilmut, I., et al., "Viable offspring derived from fetal and adult mammalian cells", *Nature*, 385:810–813 (1997).

Wolf, D.P., et al., "Nuclear transfer in the rhesus monkey: practical and basic implications," *Biology of Reproduction*, 60:199–204 (1999).

Fulka, Jr., J. and Moor, R.M., "Noninvasive chemical enucleation of mouse oocytes," *Molecular Reproduction and Development*, 34:427–430 (1993).

Procházka, R. and Fiser, P.S., "Behaviour of blastomere nuclei fused to mouse oocytes is affected by oocyte enucleation and age," *Reprod. Nutr. Dev.*, 39:695–701 (1995).

Kárníková, L., et al., "Chemically enucleated mouse oocytes: ultrastructure and kinetics of histone H1 kinase activity," *Reprod. Nutr. Dev.*, 38:643–651 (1998).

Campbell, K.H.S., "Nuclear transfer in farm animal species," *Cell & Developmental Biology*, 10:245–252 (1999).

Zawada, W.M., et al., "Somatic cell cloned transgenic bovine neurons for transplantation in parkinsonian rats," *Nature Medicine*, 4:569–574 (1998).

Stice, S.L., et al., "Cloning: new breakthroughs leading to commercial opportunities," *Theriogenology* 49:129–138 (1998).

Rampoldi, E., et al. "Cytologic and flow cytometric DNA analysis of multinucleated tumor cells and derived microcells," *Analytical and Quantitative Cytology and Histology*, 11:59–66 (1989).

Lanza, R.P., et al., "Human therapeutic cloning," *Nature Medicine*, 5:975–977 (1999).

Lanza, R.P., et al., "Prospects for the use of nuclear transfer in human transplantation," *Nature Biotechnology*, 17:1171–1174 (1999).

Cibelli, J.B., et al., "Transgenic bovine chimeric offspring produced from somatic cell–derived stem–like cells," *Nature Biotechnology*, 16:642–646 (1998).

* cited by examiner

METHODS FOR CLONING MAMMALS USING TELOPHASE OOCYTES

RELATED APPLICATION(S)

This application claims the benefit of priority to U.S. Provisional Application No. 60/149,317, filed on August 17, 1999, entitled, "Induced Enucleation Methods To Clone Non-Human Animals," by Baguisi et al.; U.S. Provisional Application No. 60/131,061, filed on Apr. 26, 1999, entitled, "Use of Telophase Oocytes to Clone Non-Human Animals," by Baguisi et al; U.S. Provisional Application No. 60/131,328, filed Apr. 26, 1999, entitled, "Transgenic and Cloned Mammals," by Baguisi, et al.; and U.S. Provisional Application No. 60/106,728, filed Nov. 2, 1998, entitled, "Transgenic and Cloned Mammals," by Echelard, et al., the entire teachings of which are incorporated herein by reference.

GOVERNMENT SUPPORT

This inventional was made with Government support under GM35395, awarded by the National Institutes of Health. The Government has certain rights in the invention.

BACKGROUND OF THE INVENTION

The production of desired proteins is useful in drug development and treatment of diseases. Several traditional methods for producing proteins, especially in high volume, are often inadequate for several reasons. Transgenic technology or cloning technology can lead to several advancements in medicine, including the production of useful proteins. Transgenic or cloning technology allows for the introduction of a transgenic nucleotide sequence into a host animal, thereby allowing for the expression of this transgenic nucleotide sequence, and production of the protein.

Accordingly, few reliable methods exist for producing transgenic or cloned animals, especially those methods that are able to produce useful proteins. Hence, a need exists for producing transgenic or cloned animals, and in particular, animals that make such desirable proteins.

SUMMARY OF THE INVENTION

The present invention provides effective methods for producing transgenic or cloned animals, and for obtaining useful proteins. The invention includes methods for cloning an animal by combining a genome from an activated donor cell with an activated, enucleated oocyte to thereby form a nuclear transfer embryo, and impregnating an animal with the nuclear transfer embryo in conditions suitable for gestation of the cloned animal. The activated donor cell is in a stage of the mitotic cell cycle such as $G_1$ phase, S phase, or $G_2/M$ phase. The activated donor cell can be a variety of cells such as a somatic cell (e.g., an adult somatic cell or an embryonic somatic cell), a germ cell or a stem cell. Types of somatic cells include fibroblast cells or epithelial cells. The activated, enucleated oocyte is in a stage of the meiotic cell cycle, such as metaphase I, anaphase I, anaphase II or telophase II. The oocyte can be enucleated chemically, by X-ray irradiation, by laser irradiation or by physical removal of the nucleus.

The invention also includes a method of producing a transgenic animal by combining a genetically engineered genome from an activated donor cell with an activated, enucleated oocyte to thereby form a transgenic nuclear transfer embryo; and impregnating an animal with the transgenic nuclear transfer embryo in conditions suitable for gestation of the transgenic animal. The stages of the cell cycle for the activated donor cell and the activated, enucleated oocyte are described above. The types of activated donor cell are also described above. The oocyte can be enucleated chemically, by X-ray irradiation, by laser irradiation or by physical removal of the nucleus.

The present invention also relates to methods of producing a nuclear transfer embryo, comprising combining a genome from an activated donor cell with an activated, enucleated oocyte. The oocyte is activated by exposing the oocyte to increased levels of calcium, and/or decreasing phosphorylation in the oocyle. Compounds or conditions that activate the oocyte are, for example, ethanol, ionophore or electrical stimulation in the presence of calcium. Increases of calcium can be between above 10% and 60% above baseline levels of calcium. The donor cell is activated by reducing the nutrients in the serum of the donor cell (e.g., 0.5% Fetal Bovine Serum) for a period of time, and then exposing the donor cell to serum having an increased amount of nutrients (10% Fetal Bovine Serum). Combining a genome from an activated donor cell with an activated oocyte can include fusing the activated donor cell with the activated oocyte, or microinjecting the nucleus of the activated donor cell into the activated oocyte.

The present invention also pertains to methods of producing a protein of interest in an animal, comprising combining a genome from an activated donor cell with an activated, enucleated oocyte to thereby form a nuclear transfer embryo, wherein the genome from the activated donor cell encodes the protein of interest; impregnating an animal with the nuclear transfer embryo in conditions suitable for gestation of a cloned animal; and purifying the protein of interest from the cloned animal. Purification of the protein of interest can be expressed in tissue, cells or bodily secretion of the cloned animal. Examples of such tissue, cells or bodily secretions are milk, blood, urine, hair, mammary gland, muscle, viscera (e.g., brain, heart, lung, kidney, pancreas, gall bladder, liver, stomach, eye, colon, small intestine, bladder, uterus and testes).

The present invention further encompasses a method of producing a heterologous protein in a transgenic animal comprising combining a genetically engineered genome from an activated donor cell with an activated, enucleated oocyte to thereby form a nuclear transfer embryo, wherein the genome from the activated donor cell encodes the heterologous protein; impregnating an animal with the nuclear transfer embryo in conditions suitable for gestation of the nuclear transfer embryo into a cloned animal; and recovering the heterologous protein from the cloned animal. The genetically engineered genome includes an operatively linked promoter (e.g., a host endogenous promoter, an exogenous promoter and a tissue-specific promoter). Examples of tissue-specific promoters are mammary-specific promoter, blood-specific promoter, muscle-specific promoter, neural-specific promoter, skin-specific promoter, hair-specific promoter and urinary-specific promoter.

The present invention also embodies methods of enucleating an oocyte having a meiotic spindle apparatus, by exposing the oocyte with a compound that destabilizes the meiotic spindle apparatus. Destabilizing the meiotic spindle apparatus results in destabilizing microtubules, chromosomes, or centrioles. Compounds that can destabilize the meiotic spindle apparatus are, for example, demecolcine, nocodazole, colchicine, and paclitaxel. To further enhance destabilization of the mieotic spindle apparatus, the temperature, osmolality or composition of medium which surrounds the oocyte can be altered.

Additionally, the invention includes methods of preparing an oocyte for nuclear transfer, comprising: exposing the oocyte to ethanol, ionophore, or to electrical stimulation, to thereby obtain an activated oocyte, and subjecting the activated oocyte to a compound that destabilizes meiotic spindle apparatus, to thereby enucleate the activated oocyte. The compounds described above destabilize the meiotic spindle apparatus. The activated oocyte can be in a stage of a meiotic cell cycle, such as metaphase I, anaphase I, anaphase II and telophase II.

The present invention advantageously allows for more efficient cloning methods. By fusing or combining an activated oocyte with the genome from an activated donor cell, the resulting nuclear transfer embryo is more competent to develop. This developmentally competent nuclear transfer embryo results in improved pregnancy rates of an animal impregnated with the nuclear transfer embryo. These animals give birth to cloned animals.

DETAILED DESCRIPTION OF THE INVENTION

The present invention relates to methods of cloning an animal by combining an activated oocyte with the genome from an activated donor cell. "Cloning an animal" refers to producing an animal that develops From an oocyte containing genetic information or the nucleic acid sequence of another animal, the animal being cloned. The cloned animal has substantially the same or identical genetic information as that of the animal being cloned. "Cloning" also refers to cloning a cell, which includes producing an oocyte containing genetic information or the nucleic acid sequence of another animal. The resulting oocyte having the donor genome is referred to herein as a "nuclear transfer embryo."

The present invention encompasses the cloning of a variety of animals. These animals include mammals (e.g., human, canines, felines), murine species (e.g., mice, rats), and ruminants (e.g., cows, sheep, goats, camels, pigs, oxen, horses, llamas). In particular, goats of Swiss origin, for example, the Alpine, Saanen and Toggenburg bread goats, were used in the Examples described herein. The donor cell and the oocyte are preferably from the same animal.

Both the donor cell and the oocyte must be activated. An activated (e.g., non-quiescent) donor cell is a cell that is in actively dividing (e.g., not in a resting stage of mitosis). In particular, an activated donor cell is one that is engaged in the mitotic cell cycle, such as $G_1$ phase, S phase or $G_2/M$ phase. The mitotic cell cycle has the following phases, $G_1$, S, $G_2$ and M. The $G_2/M$ phase refers to the transitional phase between the $G_2$ phase and M phase. The commitment event in the cell cycle, called START (or restriction point), takes place during the $G_1$ phase. "START" as used herein refers to late $G_1$ stage of the cell cycle prior to the commitment of a cell proceeding through the cell cycle. The decision as to whether the cell will undergo another cell cycle is made at START. Once the cell has passed through START, it passes through the remainder of the $G_1$ phase (i.e., the pre-DNA synthesis stage). The S phase is the DNA synthesis stage, which is followed by the $G_2$ phase, the stage between synthesis and mitosis. Mitosis takes place during the M phase. If prior to START, the cell does not undergo another cell cycle, the cell becomes arrested. In addition, a cell can be induced to exit the cell cycle and become quiescent or inactive. A "quiescent" or "inactive" cell, is referred to as a cell in $G_0$ phase. A quiescent cell is one that is not in any of the above-mentioned phases of tile cell cycle. Preferably, the invention utilizes a donor cell is a cell in the $G_1$ phase of the mitotic cell cycle.

It is preferable that the donor cells be synchronized. Using donor cells at certain phases of the cell cycle, for example, $G_1$ phase, allows for synchronization of the donor cells. One can synchronize the donor cells by depriving (e.g., reducing) the donor cells of a sufficient amount of nutrients in the media that allows them to divide. Once the donor cells have stopped dividing, then the donor cells are exposed to media (serum) containing a sufficient amount of nutrients to allow them to being dividing (e.g., mitosis). The donor cells begin mitosis substantially at the same time, and are therefore, synchronous. For example, the donor cells are deprived of a sufficient concentration of serum by placing the cells in 0.5% Fetal Bovine Serum (FBS) for about a week. Thereafter, the cells are placed in about 10% FBS and they will begin dividing at about the same time. They will enter the G1 phase about the same time, and are therefore, ready for the cloning process. See the Exemplification section for details about the synchronization of the donor cells.

Methods of determining which phase of the cell cycle a cell is in are known to those skilled in the art, for example, U.S. Pat. No. 5,843,705 to DiTullio et al., Campbell, K. H. S., et al., *Embryo Transfer Newsletter*, vol. 14(1):12–16 (1996), Campbell, K. H. S., et al., *Nature*, 380:64–66 (1996), Cibelli, J. B., et al., *Science*, 280:1256–1258 (1998), Yong, Z. and L. Yuqiang, *Biol. of Reprod.*, 58:266–269 (1998) and Wilmut, I., et al., *Nature*, 385:810–813 (1997). For example, as described below in the Examples, various markers are present at different stages of the cell cycle. Such markers can include cyclines D 1, 2, 3 and proliferating cell nuclear antigen (PCNA) for $G_1$, and BrDu to detect DNA synthetic activity. In addition, cells can be induced to enter the $G_0$ stage by culturing the cells on a serum-deprived medium. Alternatively, cells in $G_0$ stage can be induced to enter into the cell cycle, that is, at $G_1$ stage by serum activation (e.g., exposing the cells to serum after the cells have been deprived of a certain amount of serum).

The donor cell can be any type of cell that contains a genome or genetic material (e.g., nucleic acid), such as a somatic cell, germ cell or a stem cell. The term "somatic cell" as used herein refers to a differentiated cell. The cell can be a somatic cell or a cell that is committed to a somatic cell lineage. Alternatively, any of the methods described herein can utilize a diploid stem cell that gives rise to a germ cell in order to supply the genome for producing a nuclear transfer embryo. The somatic cell can originate from an animal or from a cell and/or tissue culture system. If taken from an animal, the animal can be at any stage of development, for example, an embryo, a fetus or an adult. Additionally, the present invention can utilize embryonic somatic cells. Embryonic cells can include embryonic stem cells as well as embryonic cells committed to a somatic cell lineage. Such cells can be obtained from the endoderm, mesoderm or ectoderm of the embryo. Embryonic cells committed to a somatic cell lineage refer to cells isolated on or after approximately day tell of embryogenesis. However, cells can be obtained prior to day ten of embryogenesis. If a cell line is used as a source for a chromosomal genome, then primary cells are preferred. The term "primary cell line" as used herein includes primary cells as well as primary derived cell lines.

Suitable somatic cells include fibroblasts (for example, primary fibroblasts), epithelial cells, muscle cells, cumulous cells, neural cells, and mammary cells. Other suitable cells include hepatocytes and pancreatic islets.

The genome of the somatic cell can be the naturally occurring genome, for example, for the production of cloned animals, or the genome can be genetically altered to comprise a transgenic sequence, for example, for the production of transgenic cloned animals, as further described herein.

Somatic cells can be obtained by, for example, disassociation of tissue by mechanical (e.g., chopping, mincing) or enzymatic means (e.g., trypsinization) to obtain a cell suspension followed by culturing the cells until a confluent monolayer is obtained. The somatic cells can then be harvested and prepared for cryopreservation, or maintained as a stalk culture. The isolation of somatic cells, for example, fibroblasts, is described herein.

The oocytes used in the present invention are activated oocytes. Activated oocytes are those that are in a dividing stage of meiotic cell division, and include metaphase I, anaphase I, anaphase II, and preferably, telophase II. Oocytes in metaphase II are considered to be in a resting state. The oocytes can be in the resting stage of metaphase II, and then activated, using methods described herein. The stage that the oocyte is in can be identified by visual inspection of the oocyte under a sufficient magnification. Oocytes that are in telophase II are identified, for example, by the presence of a protrusion of the plasma membrane of a second polar body. Methods for identifying the stage of meiotic cell division are known in the art.

Oocytes are activated by increasing their exposure to calcium levels. Increasing levels of calcium, e.g., by between about 10% and about 60% above the baseline levels, induces activation or meiotic cell division of the oocyte. Baseline levels are those levels of calcium found in an inactive oocyte. Rising levels of calcium, coupled with decreasing levels of phosphorylation further facilitates activation of the oocyte. Several methods exist that allow for activation of the oocyte. In particular, a calcium ionophore (e.g., ionomycin) is an agent that increases the permeability of the oocyte's membrane and allows calcium to enter into the oocyte. As the free calcium concentration in the cell increases during exposure to the ionophore, the oocyte is activated following reduction in MPF (maturation promoting factor) activity. Such methods of activation are described in U.S. Pat. No. 5,496,720. Ethanol has a similar affect. Prior to or following enucleation, an oocyte in metaphase II can be activated with ethanol according to the ethanol activation treatment as described in Presicce and Yang, *Mol. Reprod. Dev.*, 37.61–68 (1994); and Bordignon & Smith, *Mol. Reprod. Dev.*, 49:29–36 (1998). Exposure of calcium to the oocyte also occurs through electrical stimulation. The electrical stimulation allows increasing levels of calcium to enter the oocyte.

Oocytes can be obtained from a donor animal during that animal's reproductive cycle. For example, oocytes can be aspirated from follicles of ovaries at given times during the reproductive cycle (exogenous hormone-stimulated or non-stimulated). Also at given times following ovulation, a significant percentage of the oocytes, for example, are in telophase. Additionally, oocytes can be obtained and then induced to mature in vitro to arrested metaphase II stage. Arrested metaphase II oocytes, produced in vivo or in vitro can then be induced in vitro to enter telophase. Thus, oocytes in telophase can readily be obtained for use in the present invention. In particular, oocytes can be collected from a female animal following super ovulations. Oocytes can be recovered surgically by flushing the oocytes from the oviduct of a female donor. Methods of inducing super ovulations in, for example, goats and the collection of the oocytes are described herein.

Preferably, the cell stage of the activated oocytes correlates to the stage of the cell cycle of the activated donor cell. This correlation between the meiotic stage of the oocyte and the mitotic stage of the donor cell is also referred to herein as "synchronization." For example, an oocyte in telophase fused with the genome of a donor cell in $G_1$ prior to START, provides a synchronization between the oocyte and the donor nuclei in the absence of premature chromatin condensation (PCC) and nuclear envelope breakdown (NEBD).

The present invention utilizes an oocyte that is enucleated. An enucleated oocyte is one that is devoid of the genome, or one that is "functionally enucleated." A functionally enucleated oocyte contains a genome that is non-functional, e.g., cannot replicate or synthesize DNA. See, for example, Bordignon, V. and L. C. Smith, *Molec. Reprod. Dev.*, 49:29–36 (1998). Preferably, the genome of the oocyte is removed from the oocyte. A genome can be functionally enucleated from the oocyte by irradiation, by x-ray irradiation, by laser irradiation, by physically removing the genome, or by chemical means. Other known methods of enucleation can be used with the present invention to enucleate the oocyte.

The oocyte can also be rendered functionally inactive by, for example, irradiating the endogenous nuclear material in the oocyte. Methods of using irradiation are known to those in the art and are described, for example, in Bradshaw et al., *Molecul. Reprod. Dev.*, 41:503–512 (1995).

To physically remove the genome of an oocyte, one can insert a micropipette or needle into the zona pellicuda of the oocyte to remove nuclear material from the oocyte. In one example, telophase oocytes which have two polar bodies can be enucleated with a micropipette or needle by removing the second polar body in surrounding cytoplasm. Specifically, oocytes in telophase stage of meiosis can be enucleated at any point from the presence of a protrusion in the plasma membrane from the second polar body up to the formation of the second polar body itself. Thus, as used herein, oocytes which demonstrate a protrusion in the plasma membrane, usually with a spindle abutted to it, up to extrusion of a second polar body are considered to be oocytes in telophase. Methods of enucleating a oocyte are described in further detail in the Exemplification Section.

The oocyte can be rendered functionally inactive also by chemical methods. Methods of chemically inactivating the DNA are known to those of skill in the art. For example, chemical inactivation can be preformed using the ctopsoide-cycloheximide method as described in Fulka and Moore, *Molecul. Reprod. Dev.*, 34:427–430 (1993). The present invention includes enucleating the genome of an oocyte by treating the oocyte with a compound that will induce the oocyte genome (e.g., nuclear chromatin to segregate into the polar bodies during meiotic maturation thereby leaving the oocyte devoid of a functional genome, and resulting in the formation of a recipient cytoplast for use in nuclear transfer procedures. Examples of agents that will effect such differential segregation include agents that will disrupt 1) cytoskeletal structures including, but not limited to, Taxol® (e.g., paclitaxel), demecolcine, phalloidin, colchicine, nocodozole, and 2) metabolism including, but not limited to, cycloheximide and tunicamycin. In addition, exposure of oocytes to other agents or conditions (e.g. increased or decreased temperature, pH, osmolality) that preferentially induce the skewed segregation of the oocyte genome so as to be extruded from the confines of the oocyte (e.g., in polar bodies) also are included in the preferred method. See, for example, methods to include changes in the cytoskeleton and metabolism of cells, methods that are known to those in the art Andreau, J. M. and Timasheff, S. N., *Proc. Nat. Acad. Sci.* 79:6753 (1982), Obrig, T. G., et al., *J. Biol. Chem.* 246:174 (1971), Duskin, D. and Mahoney, W. C., *J. Biol. Chem.* 257:3105 (1982), Scialli, A. R., et al, *Teratogen, Carcinogen, Mutagen* 14:23 (1994), Nishiyarna, I and Fujii, T., *Exp. Cell Res.* 198:214 (1992), Small, J. V., et al, *J. Cell Sci.* 89:21 (1988), Lee, J. C., et al, *Biochem.* 19:6209 (1980).

Combination of the activated, enucleated oocyle and the genome from the activated donor cell can occur a variety of ways to form the nuclear transfer embryo. A genome of an activated donor cell can be injected into the activated oocyte by employing a microinjector (i.e., micropipette or needle). The nuclear genome of the activated donor cell, for example, a somatic cell, is extracted using a micropipette or needle. Once extracted, the donor's nuclear genome can then be placed into the activated oocyte by inserting the micropipette, or needle, into the oocyte and releasing the nuclear genome of the donor's cell. McGrath, J. and D. Solter, *Science*, 226:1317–1319 (1984).

The present invention also includes combining the genome of an activated donor cell with an activated oocyte by fusion e.g., electrofusion, viral fusion, liposomal fusion, biochemical reagent fusion (e.g., phytoheniaglutinin (PHA) protein), or chemical fusion (e.g., polyethylene glycol (PEG) or ethanol) The nucleus of the donor cell can be deposited within the zona pelliduca which contains the oocyte. The steps of fusing the nucleus with the oocyte can then be performed by applying an electric field which will also result in a second activation of the oocyte. The telophase oocytes used are already activated, hence any activation subsequent to or simultaneous with the introduction of genome from a somatic cell would be considered a second activation event. With respect to electrofusion, chambers, such as the BTX® 200 Embryomanipulation System for carrying out electrofusion are commercially available from for example BTX®, San Diego. The combination of the genome of the activated donor cell with the activated oocyle results in a nuclear transfer embryo.

A nuclear transfer embryo of the present invention is then transferred into a recipient animal female and allowed to develop or gestate into a cloned or transgenic animal. Conditions suitable for gestation are those conditions that allow for the embryo to develop and mature into a fetus, and eventually into a live animal. Such conditions are further described in the Exemplification Section, and are known in the art. For example, the nuclear transfer embryo can be transferred via the fimbria into the oviductal lumen of each recipient animal female as described in the Exemplification Section. In addition, methods of transferring an embryo to a recipient known to those skilled in the art and are described in Ebert et al., *Bio/Technology*, 12:699 (1994). The nuclear transfer embryo can be maintained in a culture system until at least first cleavage (2-cell stage) up to the blastocyst stage, preferably the embryos are transferred at the 2-cell or 4-cell stage. Various culture media for embryo development are known to those skilled in the art. For example, the nuclear transfer embryo can be co-cultured with oviductal epithelial cell monolayer derived from the type of animal to be provided by the practitioner. For example methods of obtaining goat oviductal epithelial cells (GOEC) maintaining the cells in a co-culture are described in the Examples below.

The present invention also relates to methods for generating transgenic animals by combining an activated oocyte with and a genetically engineered genome from an activated donor cell. Such a combination results in a transgenic nuclear transfer embryo. A transgenic animal is an animal that has been produced from a genome from a donor cell that has been genetically altered, for example, to produce a particular protein (a desired protein). Methods for introducing DNA constructs into the germ line of an animal to make a transgenic animal are known in the art. For example, one or several copies of the construct may be incorporated into the genome of a animal embryo by standard transgenic techniques.

Embryonal target cells at various developmental stages can be used to introduce transgenes. A transgene is a gene that produces the desired protein and is eventually incorporated into the genome of the activated oocyte. Different methods are used depending upon the stage of development of the embryonal target cell. The specific line(s) of any animal used to practice this invention are selected for general good health, good embryo yields, good pronuclear visibility in tile embryo, and good reproductive fitness. In addition, the haplotype is a significant factor.

Genetically engineered donor cells for use in the instant invention can be obtained from a cell line into which a nucleic acid of interest, for example, a nucleic acid which encodes a protein, has been introduced.

A construct can be introduced into a cell via conventional transformation or transfection techniques. As used herein, the terms "transfection" and "transformation" include a variety of techniques for introducing a transgenic sequence into a host cell, including calcium phosphate or calcium chloride co-precipitation, DEAE dextrane-mediated transfection, lipofection, or electroporation. In addition, biological vectors, for example, viral vectors can be used as described below. Samples of methods for transforming or transfecting host cells can be found in Sambrook et al, Molecular Cloning: A Laboratory Manual In Second Edition, Cold Spring Harbor Laboratory, (Cold Spring Harbor Laboratory Press, Cold Spring Harbor, N.Y. 1989). Two useful and practical approaches for introducing genetic material into a cell are electroporation and lipofection.

The DNA construct can be stably introduced into a donor cell line by electroporation using the following protocol: donor cells, for example, embryonic fibroblasts, are resuspended in phosphate buffer saline (PBS) at about $4 \times 10^6$ cells per mL. Fifty micrograms of linearized DNA is added to the 0.5 mL cell suspension, and the suspension is placed in a 0.4 cm electrode gap cuvette. Electroporation is performed using a BioRad Gene Pulser (Bio Rad) electroporator with a 330 volt pulse at 25 mA, 1000 microFarad and infinite resistance. If the DNA construct contains a neomyocin resistance gene for selection, neomyocin resistant clones are selected following incubation where 350 mg/mL of G418 (GIBCO BRL) for fifteen days.

The DNA construct can be stably introduced into a donor somatic cell line by lipofection using a protocol such as the following: about $2 \times 10^5$ cells are plated into a 3.5 cm well and transfected with 2 mg of linearized DNA using LipfectAMINE® (GIBCO BRL). Forty-eight hours after transfection, the cells are split 1:1000 and 1:5000 and if the DNA construct contains a neomyocin resistance gene for selection, G418 is added to a final concentration of 0.35 mg/mL. Neomyocin resistant clones are isolated and expanded for cyropreservation as well as nuclear transfer.

It is often desirable to express a protein, for example, a heterologous protein, in a specific tissue or fluid, for example, the milk of a transgenic animal. A heterologous protein is one that from a different species than the species being cloned. The heterologous protein can be recovered from the tissue or fluid in which it is expressed. For example, it is often desirable to express the heterologous protein in milk. Methods for producing a heterologous protein under the control of a milk-specific promoter is described below. In addition, other tissue-specific promoters, as well as, other regulatory elements, for example, signal sequences and sequences which enhance secretion of non-secreted proteins, are described below. The transgenic product (e.g., a heterologous protein) can be expressed, and therefore, recovered in various tissue, cells or bodily secretions of the transgenic animals. Examples of such tissue, cells or secretions are blood, urine, hair, skin, mammary gland, muscle, or viscera (or a tissue component thereof) including, but not limited to, brain, heart, lung, kidney, pancreas, gall bladder, liver, stomach, eye, colon, small intestine, bladder, uterus and testes. Recovery of a transgenic product from these tissues are well known to those skilled in the art, see, for example, Ausubel, F. M., et al. (eds), *Current Protocols in Molecular Biology*, vol. 2, ch. 10 (1991).

Useful transcriptional promoters are those promoters that are preferentially activated in mammary epithelial cells, including promoters that control the genes encoding protein such as caseins, β-lactoglobin (Clark et al., *Bio/Technology*, 7:487–492 (1989)), whey acid protein (Gordon et al *Bio/Technology*, 5:1183–1187 (1987)), and lactalbumin (Soulier et al., *Febs Letts.*, 297:13 (1992)). Casein promoters may be derived from the alpha, beta, gamma, or kappa casein genes of any animal species; a preferred promoter is derived from tile goat β-casein gene (Ditullio, *Bio/Technology*, 10:74–77 (1992)). Milk specific protein promoter or the promoters that are specifically activated in mammary tissue can be derived from cDNA or genomic sequences.

DNA sequence information is available for the mammary gland's specific genes listed above, in at least one, and often in several organisms. See, for example, Richards et al., *J. Biol. Chem.*, 256:526–532 (1981) (α-Lactalbumin rat); Campbel et al., *Nucleic Acids Res.*, 12:8685–8697 (1984) (rat WAP); Jones et al., *J. Biol. Chem.*, 260:7042–7050 (1985) (rat β-Casein); Yu-Lee and Rosen, *J. Biol. Chem.*, 258:10794–10804 (1983) (rat α-Casein); Hall, *Bio. Chem. J.*, 242:735–742 (1987); (α-Lactalbumin human); Stewart, *Nucleic Acids Res.*, 12:389 (1984) (Bovine α S1 and κ1 Casein, cDNAs); Gorodetsky et al., *Gene*, 66:87–96 (1988) (Bovine β-Casein); Alexander et al., *Eur. J. Biochem.*, 178:395–401 (1988) (Bovine and κ-Casein); Brignon et al., *Febs Let.*, 188:48–55 (1977) (Bovine α S2 Casein); Gamieson et al., *Gene*, 61:85–90 (1987); Ivanov et al., *Biol. Chem. Hopp-Seylar*, 369:425–429 (1988); Alexander et al., *Nucleic Acid Res.*, 17:6739 (1989) (Bovine β-Lactoglobulin); Vilotte et al., *Biochimie*, 69:609–620 (1987) (Bovine α-Lactalbumin).

The structure and function of the various milk protein genes are reviewed by Mercier & Vilotte, *J. Dairy Sci.*, 76:3079–3098 (1993). If additional flanking sequences are useful in optimizing expression of tile heterologous protein, such sequences can be cloned using the existing sequences as probes. Mammary gland specific regulatory sequences from different organisms can be obtained by screening libraries from such organisms using known cognate nucleotide sequences or antibodies to cognate proteins as probes.

Useful signal sequences such is milk specific signal sequences or other signal sequences which result in the secretion of eucaryotic or prokaryotic proteins can be used. Preferably, the signal sequence is selected from milk specific signal sequences, that is, it is from a gene which encodes a product secreted into milk. Most preferably, the milk specific signal sequence is related to the milk specific promoter used in the construct. The size of the signal sequence is not critical. All that is required is that the sequence be of a sufficient size to effect secretion of the desired recombinant protein, for example, in the mammary tissue. For example, signal sequences from genes coding for caseins, for example, α, β, γ or κ caseins and the like can be used. A preferred signal sequence is the goat β-casein signal sequence. Signal sequences from other secreted proteins, for example, proteins secreted by kidney cells, pancreatic cells, or liver cells, can also be used. Preferably, the signal sequence results in the secretion of proteins into, for example, urine or blood.

A non-secreted protein can also be modified in such a manner that it is secreted such as by inclusion in the protein to be secreted all or part of the coding sequence of a protein which is normally secreted. Preferably, the entire sequence of the protein which is normally secreted is not included in the sequence of the protein but rather only a sufficient portion of the amino terminal end of the protein which is normally secreted to result in secretion of the protein. For example, a portion which is not normally secreted is fused (usually at its amino terminal end) to an amino terminal portion of the protein which is normally secreted.

In one aspect, the protein which is normally secreted is a protein which is normally secreted in milk. Such proteins include proteins secreted by mammary epithelial cells, milk proteins such as caseins, β-lactoglobulin, whey acid protein, and lactalbumin. Casein proteins including, alpha, beta, gamma or kappa casein genes of any mammalian species. The preferred protein is β-casein, for example, goat β-casein. Sequences which encode the secreted protein can be derived from either cDNA or genomic sequences. Preferably, they are of genomic origin, and include one or more introns.

Other tissue specific promoters which provide expression in a particular tissue can be used. Tissue specific promoters are promoters which are expressed more strongly in a particular tissue than in others. Tissue specific promoters are often expressed exclusively in the specific tissue.

Tissue specific promoters which can be used include: a neural-specific promoter, for example, nestin, Wnt-1, Pax-1, Engrailed-1, Engrailed-2, Sonic-hedgehog: a liver specific promoter, for example, albumin, alpha-1, antitrypsin; a muscle-specific promoter, for example, myogenin, actin, MyoD, myosin; an oocyte specific promoter, for example, ZP1, ZP2, ZP3; a testus specific promoter, for example, protamine, fertilin, synaptonemal complex protein-1; a blood specific promoter, for example, globulin, GATA-1, porphobilinogen deaminase; a lung specific promoter, for example, surfactin protein C; a skin or wool specific promoter, for example, keratin, elastin; endothelium-specific promoter, for example, TIE-1, TIE-2; and a bone specific promoter, for example, BMP. In addition, general promoters can be used for expression in several tissues. Examples of general promoters, include β-actin, ROSA-21, PGK, FOS, c-myc, Jun-A, and Jun-B.

A cassette which encodes a heterologous protein can be assembled as a construct which includes a promoter for a specific tissue, for example, for mammary epithelial cells, a casein promoter. The construct can also include a 3' untranslated region downstream of the DNA sequence coding for the non-secreted proteins. Such regions can stabilize the RNA transcript of the expression system and thus increase the yield of desired protein from the expression system. Among the 3' untranslated regions useful in the constructs for use in the invention are sequences that provide a polyA signal. Such sequences may be derived, for example, from the SV40 small t antigen, the casein 3' untranslated region or other 3' untranslated sequences well known in the art. In one aspect, the 3' untranslated region is derived loon a milk specific protein. The length of the 3' untranslated region is not critical but the stabilizing effect of its polyA transcript appears imported in stabilizing the RNA of the expression sequence.

Optionally, the construct can include a 5' untranslated region between the promoter and the DNA sequence encoding the signal sequence. Such untranslated regions can be from the same control region as that from which the promoter is taken or can be from a different gene, for example, they may be derived from other synthetic, semisynthetic or natural sources. Again, there specific length is not critical, however, they appear to be useful in improving the level of expression.

The construct can also include about 10%, 20%, 30% or more of the N-terminal coding region of a gene preferentially expressed in mammary epithelial cells. For example, the N-terminal coding region can correspond to the promoter used, for example, a goat β-casein N-terminal coding region.

The construct can be prepared using methods known to those skilled in the art. The construct can be prepared as part of a larger plasmid. Such preparation allows the cloning and selection of the correct constructions in an efficient manner. The construct can be located between convenient restrictions sites on the plasmid so that they can be easily isolated from the remaining plasmid sequences for incorporation into the desired animal.

Transgenic sequences encoding heterologous proteins can be introduced into the germ line of an animal or can be transfected into a cell line to provide a source of genetically engineered donor cells as described above. The protein can be a complex or multimeric protein, for example, a homo-or hetromultimeric proteins. The protein can be a protein which is processed by removing the N-terminus, C-terminus or internal fragments. Even complex proteins can be expressed in active form. Protein encoding sequences which can be introduced into the genome of an animal, for example, goats, include glycoproteins, neuropeptides, immmunoglobulins, enzymes, peptides and hormones. The protein may be a naturally occurring protein or a recombinant protein for example, a fragment or fusion protein, (e.g., an immunoglobulin fusion protein or a mutien). The protein encoding nucleotide sequence can be human or non-human in origin. The heterologous protein may be a potential therapeutic or pharmaceutical agent such as, but not limited to, alpha-1 proteinase inhibitor, alpha-1 antitrypsin, alkaline phosphatase, angiogenin, antithrombin III, any of the blood clotting factors including Factor VIII, Factor IX, and Factor X chitinase, erytilropoietin, extracellular superoxide dismutase, fibrinogen, glucocerebrosidas, glutamate decarboxylase, human growth factor, human serum albumin, immunoglobulin, insulin, myelin basic protein, proinsulin, prolactin, soluble CD 4 or a component or complex thereof, lactoferrin, lactoglobulin, lysozyme, lactalbumin, tissue plasminogen activator or a variant thereof. Immunoglobulin particularly preferred protein. Examples of immunoglobulins include IgA, IgG, IgE, IgM, chimeric antibodies, humanized antibodies, recombinant antibodies, single chain antibodies and anti-body protein fusions.

Nucleotide sequence information is available for several of the genes encoding the heterologous proteins listed above, in at least one, and often in several organisms. See, for example, Long et al., *Biochem.*, 23(21):4828–4837 (1984) (Alpha-1 antitrypsin); Mitchell et al., *Prot. Natl. Acad. Sci. USA*, 83:7182–7186 (1986) (Alkaline phosphatase); Schneider et al., *Embo J.*, 7(13): 4151–4156 (1988) (Angiogenin); Bock et al., *Biochem.*, 27 (16):6171–6178 (1988) (Antithrombin); Olds et al., *Br. J. Haematol.*, 78(3): 408–413 (1991) (Antithrombin III); Lyn et al., *Proc. Natl. Acad. Sci. USA*, 82(22):7580–7584 (1985) (erythropoietin); U.S. Pat. No. 5,614,184 (erythropoietin) Horowtiz, et al., *Genomics*, 4(1):87–96 (1989) (Glucocerebrosidase); Kelly et al., *Ann. Hum. Genet.*, 56(3):255–265 (1992) (Glutamate decarboxylase); U.S. Pat. No. 5,707,828 (human serum albumin); U.S. Pat. No. 5,652,352 (human serum albumin); Lawn et al., *Nucleic Acid. Res.*, 9(22):6103–6114 (1981) (human serum albumin); Kamholz et al., *Prot. Matl. Acad. Sci. USA*, 83(13):4962–4966 (1986) (myelin basic protein); Hiraoka et al., *Mol. Cell Endocrinol.*, 75(1):71–80 (1991) (prolactin); U.S. Pat. No. 5,571,896 (lactoferrin), Pennica et al., *Nature*, 301(5897):214–221 (1983) (tissue plasminogen activator); Sarafanov et al., *Mol. Biol.*, 29: 161–165 (1995).

A transgenic protein can be produced in the transgenic cloned animal at relatively high concentrations and in large volumes, for example in milk, providing continuous high level output of normally processed protein that is easily harvested from a renewable resource. There are several different methods known in the art for isolation of proteins for milk.

Milk proteins usually are isolated by a combination of processes. Raw milk first is fractionated to remove fats, for example by skimming, centrifugation, sedimentation, (H. E. Swaisgood, Development in Dairy Chemistry, 1: Chemistry of Milk Protein, Applied Science Publishers, NY 1982), acid precipitation (U.S. Pat. No. 4,644,056) or enzymatic coagulation with rennin or chymotrypsin (Swaisgood, ibid.). Next the major milk proteins may be fractionated into either a clear solution or a bulk precipitate from which this specific protein of interest may be readily purified.

French Pat. No. 2487642 describes the isolation of milk proteins from skim milk or whey by performing ultra filtration in combination with exclusion chromatography or ion exchange chromatography. Whey is first produced by removing the casein by coagulation with rennet or lactic acid. U.S. Pat. No. 4,485,040 describes the isolation of an cc-lactoglobulin-enriched product in the retentate from whey by two sequential ultra filtration steps. U.S. Pat. No. 4,644,056 provides a method for purifying immunoglobulin from milk or colostrum by acid precipitation at pH 4.0–5.5, is sequential cross-flow filtration first oil a membrane with 0.1–1.2 mm pore size to clarify the product pool and then on a membrane with a separation limit of 5–80 kD to concentrate it. Similarly, U.S. Pat. No. 4,897,465 teaches the concentration and enrichment of a protein such as immunoglobulin from blood serum, egg yolks or whey by sequential ultra filtration on metallic oxide membranes with a pH shift. Filtration is carried out first at a pH below the isoelectric point (pI) of the selected protein to remove bulk contaminants from the protein retenitate, in next adding pH above the pl of the selected protein to retain impurities and pass the selected protein to the permeate. A different filtration concentration method is taught by European Pat. No. EP 467 482 B1 in which defatted skim milk is reduced to pH 3–4, below the pi of the milk proteins, to solubilize both casein and whey proteins. Three successive rounds of ultra filtration are diafiltration and concentrate the proteins to form a retentate containing 15–20% solids of which 90% is protein. Alternatively. British Patent Application No. 2179947 discloses the isolation of lactoferrin from whey by ultra filtration to concentrate the sample, fall by week cation exchange chromatography at approximately a neutral pH. No measure of purity is reported in PC Publication No. WO 95/22258, a protein such as lactoferrin is recovered from milk that has been adjusted to high ionic strength by the addition of concentrated salt, followed by cation exchange chromatography.

In all these methods, milk or a fraction thereof is first treated to remove fats, lipids, and other particular matter that would foul filtration membranes or chromatography medium. The initial fractions thus produce can consist of casein, whey, or total milk protein, from which the protein of interest is then isolated.

PCT Patent Publication No. WO 94/19935 discloses a method of isolating a biologically active protein from whole milk by stabilizing the solubility of total milk proteins with a positively charged agent such as arginine, imidazole or Bis-Tris. This treatment forms a clarified solution from which the protein may be isolated for example by filtration through membranes that otherwise would become clogged by precipitated proteins.

Methods for isolating a soluble milk component such as a peptide in its biologically active form from whole milk or a milk fraction by tangential flow filtration are known. Unlike previous isolation methods, this eliminates the need for a first fractionation of whole milk to remove fat micelles, thereby simplifying the process in avoiding losses of recovery of bioactivity. This method may be used in combination with additional purification steps to further remove contaminants and purify the product (e.g., the protein of interest).

Another aspect of the present invention includes methods for enucleating an activated oocyte comprising contacting the oocyte with a compound that destabilizes (e.g., disrupts or disassociates) the meiotic spindle apparatus. Disruption of the meiotic spindle apparatus results in disruption of microtubules, chromosomes and centrioles. Such a compound renders the nucleus non-frictional. Examples of such compounds are cochicine, pactiltaxel, nocodazole and preferably, demecolcine.

This aspect of the invention can be used for enucleation in combination with the methods described herein. For example, an activated oocyte can be prepared for nuclear transfer by activating the oocyte (e.g., exposing the oocyte to ethanol or an ionophore), and then subjecting the activated oocyte to a compound that destabilizes the meiotic spindles (e.g., demecolcine). Once the activated oocyte is prepared, then it can be combined with genome from an activated donor cell to result in a nuclear transfer embryo.

The following examples are intended to be illustrative and not limiting in any way.

EXEMPLIFICATION

EXAMPLE 1

Cloning Mice Using an Induced Enucleation Method

Advances in somatic cell nuclear transfer (NT) methodology have seen the procession of cloned sheep, cows, mice and goats. Despite the clear potential use of this technology for genetic manipulations, the success rates remain woefully low. The limitations associated with nuclear transfer include the selection and preparation of competent donor cytoplasts. The cytoplasm plays a vital role in genome reprogramming and reactivation and therefore manipulations that compromise oocyte developmental competence are detrimental to the success of nuclear transfer. The present study was directed towards determining alternative methods to more efficiently prepare competent cytoplasts for nuclear transfer procedures. In experiment 1, in vivo-produced mouse metaphase II oocytes (B6D2, auguti, recovered at 16–20 h post hCG) were activated by exposure to either 7% ethanol or 2 µm ionomycin in PBS+10% FBS (5 min.). At the onset of initial second polar body formation (10–15 min. post activation) and extrusion (anaphase/telophase stage), oocytes were randomly allocated to control (cultured 0.5–1.5 h) or incubated with Taxol® (5 µg/ml), Cycloheximide (10 µg/ml) or in Demecolcine (0.4 µg/ml) in PBS+ 10% FBS until the second polar body was extruded (0.5–1.5 h post activation) to induce nuclear chromatin enucleation. Oocytes were stained (H33342, 5 µg/ml) to confirm the extent of nuclear chromatin enucleation using fluorescence microscopy. The rate of treatment-induced chromatin enucleation was 3.7% (0–15%) for control, 3.6% (0–10%) for Taxol®, 16.3% (0–24%) for Cycloheximide and 54% (27–70%) for Demecolcine treatments. In experiment 2, Demecolcine-induced enucleated cytoplasts were used for nuclear transfer recipients. Donor nuclei were prepared from cumulus cells (Black Swiss) by partial lysis (1% sodium citrate) followed by aspiration using the injection pipette (7 um). Donor nuclei were injected into cytoplasts pretreated with Cytochalasin-B (5 µg/ml, 15 min.). Reconstructed NT embryos were subsequently co-cultured (72–96 h) with oviductal cells in drops of M-199+10% FBS. The cleavage rate was 70% (85/121) and the rate of blastocyst formation was 42% (51/121). Pregnancies were established in 2/3 recipients (CD1, white) following uterine embryo transfer (10 embryos/recipient). A total of 14 black female pups were born (47%, 14/30), seven of which were stillborn from 1 recipient and the other seven were born live (23%, 7/30) but 3 were cannibalized within 24 h. The 4 cloned pups were normal and healthy, and their fertility is being assessed. These data suggest that cytoskeleton modifying agents can induce enucleation of nuclear chromatin at acceptable rates without physical perturbation associated with mechanical enucleation and with no loss of cytoplasm. Moreover, cytoplasts derived from this enucleation procedure are competent to support genome reactivation and fetal development to term. This technically simple approach may provide a more efficient method to produce large numbers of cytoplasts for cloning procedures.

EXAMPLE 2

Cloning a Transgenic Goat

Donors and recipients used in the following examples were dairy goats of the Following breeds (mixed or not): Alpine, Saanen, and Toggenburg. Collections and transfers were completed during the spring and early summer (off-season).

Isolation of Caprine Somatic Cells

Caprine fetal fibroblast cell lines used as karyoplast donors were derived from six day 35–40 fetuses produced by artificially inseminating non-transgenic does with fresh collected semen from a transgenic antithrombin III (ATIII) founder buck. An ATIII cell line was chosen since it provides a well characterized genetic marker to the somatic cell lines, and it targets high level expression of a complex glycosylated protein (ATIII) in the milk of lactating does. Three fetuses which were derived from the semen of the transgenic ATIII buck were surgically removed at day 40 post coitus and placed in equilibrated $Ca^{++}/Mg^{++}$-free phosphate buffered saline (PBS). Cell suspensions were prepared by mincing and digesting fetal tissue in 0.025% trypsin/0.5 mM EDTA at 37° C. for ten minutes. Cells were washed with equilibrated Medium 199™ (M199)(Gibco)+10% Fetal Bovine Serum (FBS) supplemented with nucleosides, 0.1 mM 2-mercaptoethanol, 2 mM L-glutamine, 1% penicillin/streptomycin (10,000 U.U. each/ml) (fetal cell medium), and cultured in 25 cm² flasks. The cultures were re-fed 24 hours later with equilibrated fetal cell medium. A confluent monolayer of primary fetal cells was harvested by trypsinization on day four by washing the monolayer twice with $Ca^{++}$/$Mg^{++}$-free PBS, followed by incubation with 0.025% trypsin/0.5 mM EDTA at 38° C. for 7 minutes.

Cells potentially expressing ATIII were then prepared for cryopreservation, or maintained as stock cultures.

Sexing and Genotyping of Donor Cell Lines

Genomic DNA was isolated from fetal head tissue for ATIII donor karyoplasts by digestion with proteinase K followed by precipitation with isopropanol as described in Laird et al. (1991) *Nucleic Acid Res.* 19:4293, and analyzed by polymerase chain reaction (PCR) for the presence of human Antithrombin III (ATIII) sequences. The ATIII sequence is part of the BC6 construct (Goat Beta-casein—humanATIII cDNA) used to generate the ATIII transgenic line as described in Edmunds et al. (1998) *Blood* 91:4561–4571. The human ATIII sequence was detected by amplification of a 367 bp sequence with oligonucleotides GTC11 and GTC12 (see below). For sexing, the zfX/zfY primer pair was used (see below) giving rise to a 445 pb (zfX)/447 bp (sfy) doublet. Upon digestion with the restriction enzyme Sac1 (New England Biolabs), the zfX band was cut into two small fragments (272 and 173 bp). Males were identified by the presence of the uncut 447 bp zfY band.

For the PCR reactions, approximately 250 ng of genomic DNA was diluted in 50 nil of PCR buffer (20 mM Tris pH 8.3, 50 mM KC1 and 1.5 mM $MgCl_2$, 0.25 mM deoxynucleotide triphosphates, and each primer at a concentration of 600 mM with 2.5 units of Taq polymerase and processed using the following temperature program.

| 1 cycle at | 94° C. | 60 seconds |
| 5 cycles at | 94° C. | 30 seconds |
| | 58° C. | 45 seconds |
| | 74° C. | 45 seconds |
| 30 cycles at | 94° C. | 30 seconds |
| | 55° C. | 30 seconds |
| | 74° C. | 30 seconds |

The following primer set was used to detect the human ATIII sequence:

GTC 11: CTCCATCAGTTGCTGGAGGGTGTCATTA (SEQ ID NO: 1)

GTC 12: GAAGGTTTATCTTTTGTCCTTGCTGCTCA (SEQ ID NO: 2)

The following primer set was used for sexing:

zfX: ATAATCACATGGAGAGCCACAAGC (SEQ ID NO: 3)

zfY: GCACTTCTTTGGTATCTGAGAAAG (SEQ ID NO: 4)

Two of the fetuses were identified to be male and were both negative for the ATIII sequence. Another fetus was identified as female and confirmed positive for the presence of the ATIII sequence.

Preparation of ATIII-Expressing Donor Cells for Embryo Reconstitution

A transgenic female line (CFF155-92-6) originating from a day 40 fetus was identified by PCR analyses, as described above, and used for all nuclear transfer manipulations. Transgenic fetal fibroblast cells were maintained in 25 $cm^2$ flasks with fetal cell medium, re-fed on day four following each passage, and harvested by trypsinization on day seven. From each passage, a new 25 $cm^2$ flasks was seeded to maintain the stock culture. Briefly, fetal cells were seeded in 4-well plates with fetal cell medium and maintained in culture (5% $CO_2$ at 39° C.), forty-eight hours later, the medium was replaced with fresh fetal cell medium containing 0.5% FBS. The culture was re-fed every 48–72 hours over the next seven days with fresh fetal cell medium containing 0.5% FBS. On the seventh day following first addition of fetal cell medium (0.5% FBS), somatic cells used as karyoplast donors were harvested by trypsinization as previously described. The cells were resuspended in equilibrated M199+10% FBS supplemented with 2 mM L-glutamine, 1% penicillin/streptomycin (10,000 I.U. each/ml) one to three hours prior to fusion to the enucleated oocytes.

Karyotyping of Cell Lines

The clonal lines were further evaluated by karyotyping to determine gross chromosomal abnormalities in the cell lines. Cells were induced to arrest at metaphase by incubation with 0.02 µg/ml of Demecolcine (Sigma) for 12 hours. After trypsinization, the resulting pellet was suspended in a hypotonic solution of 75 mM KCl in water and incubated at 37° C. for 20 minutes. Cells were fixed for 5 minutes each time in 3 changes of ice-cold acetic acid-methanol (1:3) solution before drops of the cell suspension were place din prewashed microscopic slides. Following air-drying, chromosome preparations were stained with 3% Giemsa stain (Sigma) in PBS for 10 minutes. The chromosome spreads were counted for each cell line at 1000× magnification under oil immersion.

Immunohistochemical Analysis

Antibodies specific for vimentin (Sigma) and pan-cytokeratin (Sigma) were used to characterize and confirm the morphology of the cell lines. Cells were plated in sterile gelatin coated cover slips to 75% confluence and fixed in 2% paraformaldehyde with 0.05% saponin for 1 hour. Cells were incubated in 0.5% PVP in PBS (PBS/PVP) with primary antibodies for 2 hours at 37° C., rinsed with 3 changes of PBS/PVP at 10 minute intervals, and incubated for 1 hour in secondary antibodies conjugated with Cy3 and FITC respectively. Alkaline phosphatase (Sigma) activity of the cells was also performed to determine the presence or absence of undifferentiated cells. The coverslips were rinsed and subsequently mounted on glass slides with 50% glycerol in PBS/PBP with 10 µg/ml bisbenzimide (H-33342, Sigma) and observed under fluorescent microscopy.

Epithelial and fibroblast lines positive for Fimentin and pan-cytokeratin, respectively, and negative for alkaline phosphatase activity were generated from the ATIII primary cultures. In the cell cultures, two morphologically distinct cell types were observed. Larger "fibroblast-like" cells stained positive for vimentin and smaller "epithelial-like" cells stained positive for pan-cytokeratin which coexisted in the primary cell cultures. The isolated Fibroblast lines from ATIII showed a tendency to differentiate into epithelial-like cells when cultured for 3 days after reaching confluency. Subsequent passages induced selection against fibroblast cells giving rise to pure epithelial cells as confirmed by the lick of positive staining for vimentin. Senesces or possible cell cycle arrest was first observed at passage 28. These cells appear bigger in size (>30 µm) compared to the normally growing cells (15–25 µm) and can be maintained in culture in the absence of apparent mitotic activity for several months without loss of viability. Embryo reconstruction using nuclei from the arrested cells produced morula stage embryos suggesting reacquisition of mitotic activity.

Donor Karyoplast Cell Cycle Synchronization and Characterization

Selected diploid transgenic female cell lines were propagated, passaged sequentially and cyrobanked as future karyoplast stock. Donor karoplasts for nuclear transfer were seeded in 4 well plates and cultured for up to 48 hours in DMEM+10% FBS or when cells reached 70–80% confluency. Subsequently, the cells were induced to exit growth phase and enter the quiescent stage ($G_0$) by serum deprivation for seven days using DMEM supplemented with 0.5% FBS to synchronize the cells. Following synchronization at $G_0$, a group of cells were induced to re-enter the cell cycle by resuspending the cells in M199+10% FBS up to three hours prior to karyoplast-cytoplast fusion to synchronize the cells at the early $G_1$ phase prior to START. A second group of cells were also released from the quiescent state and cultured in M199+10% FBS for 12 or 36 hours to synchronize cells at the S-phase. Cells were harvested by standard trypsinization and resuspended in M 199+10% FBS and electrofused as karyoplasts donors within 1 hour.

The metaphase spreads from the transgenic cell lines carrying the ATIII construct at passage 5 was 81% diploid and this did not alter significantly at passage 15 where 78% of the spreads were diploid.

Cell cycle synchrony was determined by immunohistochemical analysis using antibodies against cyclin D1, 2, 3 and PCNA (Oncogene Research Products) for the absence of protein complex to indicate quiescence ($G_0$) or presence of tile complex to indicate $G_1$ entry. Cells in the presumed S-phase of the cell cycle were identified by the presence of DNA synthetic activity using the thymidine analog 5-bromo 2'-deoxyuridine-5'triphospate (BrDu, Sigma) and streptavidin-Biotin BrDu staining kit (Oncogene Research Products).

Immunofluorescence analysis of cells subjected to the synchronization regimen demonstrated that following seven days of serum deprivation, 90% of the cells were negative for $G_1$ stage cyclins D1, 2, 3 and PNCA, and were therefore in $G_0$ arrest. Restoration of the serum content to 10%, for this line induced reentry into the cell cycle with approximately 74% of the cells reaching early $G_1$ within 3 hours following serum addition based on positive staining for cyclin D1. Serum restoration for 12 and 36 hours showed that 89% of the cells were positive for BrDu indicating DNA synthetic activity. In this study, clonal lines generally responded differently to the serum synchronization regimen. An indirect relationship was observed where the rate of cell synchronization decreases with the increase in passage numbers. Further, as passage number increased the population doubling times decreased, each clonal cell line revealed a decreased sensitivity to serum synchronization of the cell cycle.

Superovulation of Donor Goats and Oocyte Collection

Estrus was synchronized on day 0 by a 6 mg subcutaneous Norgestomet ear implant (Synchro-mate B). A single injection of prostaglandinn (PGF2α) (Upjohn US) was administered on day 7. Starting on day 12, FSH (Folltropin-V, Vetrepharm, St. Laurent, Quebec, Canada) was administered twice daily over four consecutive days. The ear implant was removed on day 14. Twenty-four hours following implant removal, the donor animals were mated several times to vasectomized males over a 48 hour interval. A single injection of GnRH (Rhone-Merieux US) was administered intramuscularly following the last FSH injection. Oocytes were recovered surgically from donor animals by mid-ventral laparotomy approximately 18 to 24 hours following the last mating, by flushing the oviduct with $Ca^{++}/Mg^{++}$-free PBS prewarmed at 37° C. Oocytes were then recovered and cultured in equilibrated M199+10% FBS supplemented with 2 mM L-glutamine, 1% penicillin/streptomycin (10,000 I.U. each/mil).

Oocyte Enucleation

In vivo matured oocytes were collected from donor goats. Oocytes with attached cumulus cells or devoid of polar bodies were discarded. Cumulus-free oocytes were divided into two groups: oocytes with only one polar body evident (metaphase II stage) and the activated telophase II protocol (oocytes with one polar body and evidence of an extruding second polar body). Oocytes in telophase II were cultured in M199+10% FBS for 3 to 4 hours. Oocytes that had activated during this period, as evidenced by a first polar body and a partially extruded second polar body, were grouped as culture induced, calcium activated telophase II oocytes (Telophase II-$Ca^{+2}$) and enucleated. Oocytes that had not activated were incubated for 5 minutes in PBS containing 7% ethanol prior to enucleation. Metaphase II stage oocytes (one polar body) were enucleated with a 25–30 micron glass pipette by aspirating the first polar body and adjacent cytoplasm surrounding the polar body (approximately 30% of the cytoplasm) presumably containing metaphase plate.

As discussed above, telophase stage oocytes were prepared by two procedures. Oocytes were initially incubated in phosphate buffered saline (PBS, $Ca^{+2}/Mg^{+2}$ free) supplemented with 5% FBS for 15 minutes and Cultured in M 199+10% FBS at 38° C. for approximately three hours until the telophase spindle configuration or the extrusion of the second polar body was reached. All the oocytes that responded to the sequential culture under differential extra-cellular calcium concentration treatment were separated and grouped as Telophase II-$Ca^{2+}$. The other oocytes that did not respond were further incubated in 7% ethanol in M199+10% FBS for 5–7 minutes (Telophase II-ETOH) and cultured in M199+10% FBS for 2 to 4 hours. Oocytes were then cultured in M199+10%/ FBS containing 5 μg/ml of cytochalasin-B for 10–15 minutes at 38° C. Oocytes were enucleated with a 30 micron (OD) glass pipette by aspirating the first polar body and approximately 30% of the adjacent cytoplasm containing the metaphase II or about 10% of the cytoplasm containing the telophase II spindle. After enucleation the oocytes were immediately reconstructed.

Embryo Reconstruction

CFF 155-92-6 somatic cells used as karyoplast donors were harvested on day 7 by trypsinizing (0.025% trypsin/0.5 mM EDTA) (Sigma) for 7 minutes. Single cells were resuspended in equilibrated M199+10% FBS supplemented with 2 mM L-glutamine, penicillin/streptomycin. The donor cell injection was carried out inn the same medium as for enucleation. Donor cells were graded into small, medium and large before selection for injection to enucleated cytoplasts. Small single cells (10–15 micron) were selected with a 20–30 micron diameter glass pipette. The pipette was introduced through the same slit of the zona made during enucleation and donor cells were injected between the zone pellucida and the ooplasmic membrane. The reconstructed embryos were incubated in M199 30–60 minutes before fusion and activation.

Fusion and Activation

All reconstructed embryos (ethanol pretreatment or not) were washed in fusion buffer (0.3 M mannitol, 0.05 mM $CaCl_2$, 0.1 mM $MgSO_{4-}$, 9 mM $K_2HPO^4$, 0.1 mM glutathione, 0.1 mg/ml BSA in distilled water) for 3 minutes before electrofusion. Fusion and activation were carried out at room temperature, in a chamber with two stainless steel electrodes 200 microns apart (BTX® 200 Embryomanipulation System, BTX®-Genetronics, San Diego, Calif.) filled with fusion buffer. Reconstructed embryos were placed with a pipette in groups of 3–4 and manually aligned so the cytoplasmic membrane of the recipient oocytes and donor CFF155-92-6 cells were parallel to the electrodes. Cell fusion and activation were simultaneously induced 32–42 hours post GnRH injection with an initial alignment/holding pulse of 5–10 V AC for 7 seconds, followed by a fusion pulse of 1.4 to 1.8 KV/cm DC for 70 microseconds using an Electrocell Manipulator and Enhancer 400 (BTX®-Genetronics). Embryos were washed in fusion medium for 3 minutes, then they were transferred to M199 containing 5 µg/ml cytochalasin-B (Sigma) and 10% FBS and incubated for 1 hour. Embryos were removed from M199/cytochalasin-B medium and co-cultured in 50 microliter drops of M199 plus 10% FBS with goat oviductal epithelial cells overlaid with paraffin oil. Embryo cultures were maintained in a humidified 39° C. incubator with 5% $CO_2$ for 48 hours before transfer of the embryos to recipient does.

Reconstructed embryos at 1 hour following simultaneous activation and fusion with $G_0$, $G_1$ and S-phase karyoplasts all showed nuclear envelope breakdown (NEBD) and premature chromosome condensation (PCC) when the cytoplasts were at the arrested metaphase II stage. Subsequent nuclear envelope formation was observed to be at about 35% at 4 hour post activation. Oocytes reconstructed at telophase II stage showed that an average of 22% of oocytes observed at 1 hour post fusion of $G_0$, $G_1$ and S-phase karyoplast underwent NEBD and PCC, whereas the remaining oocytes have intact nuclear lamina surrounding the decondensing nucleus. No consistent nuclear morphology other than lack of, or the occurrence of NEBD and PCC was observed between the metaphase and two telophase reconstruction protocols employed. Differences became evident when cloned embryos were observed to have a higher incidence of advanced cleavage stages (8 to 32 blastomeres) when embryos were reconstructed with S-phase donor nuclei compared to when $G_0$ or $G_1$ stage karyoplasts were used (2 to 8 blastomeres) following culture in vitro for 36 to 48 hours. Fluorescent microscopy analysis showed that the nuclei of some of the rapidly dividing embryos were fragmented. Other embryos developed to the 32 to 64 cell stage within 3 days of culture before cleavage development was blocked. Analysis of blastomere and nuclei numbers of these embryos showed the failure of synchronous occurrence of cytokines and karyokinesis wherein blastomeres were either devoid or their corresponding nuclei or contained multiple nuclei. In contrast, morphologically normal looking embryos showed synchronous cytokinesis and karyokinesis.

Goat Oviductal Epithelial Cells (GOEC) Reconstructed Embryo Co-culture

GOEC were derived from oviductal tissue collected during surgical oviductal flushing performed on synchronized and superovulated does. Oviductal tissue from a single doe was transferred to a sterile 15 ml polypropylene culture tube containing 5 ml of equilibrated M199, 10% FBS, 2 mM L-glutamine, penicillin/strepomycin. A single cell suspension was prepared by vortex mixing for 1 minute, followed by culture in a humidified 5% $CO_2$ incubator at 38° C. for up to one hour. The tube was vortex mixed a second time for one minute, then cultured an additional five minutes to allow debris to settle. The top four millimeters containing presumed single cells was transferred to a new 15 ml culture tube and centrifuge at 600×g for 7 minutes, at room temperature. The supernatant was removed, and the cell pellet resuspended in 8 ml of equilibrated GOEC medium. The GOEC were cultured in a 25 cm² flask, re-fed on day 3, and harvested by trypsinization on day six, as previously described. Monolayers were prepared weekly, from primary GOEC cultures, for each experiment. Cells were resuspended in GOEC medium at $5\times10^5$/ml, and 50 microliter/well was seeded in 4–2311 plates (15 mm). The medium was overlaid with 0.5 ml light paraffin oil, and the plates were cultured in a humidified 5% $CO_2$ incubator at 38° C. The cultures were re-fed on day two with 80% fresh equilibrated culture medium. All reconstructed embryos were co-cultured with the GOEC monolayers in vitro in incubator at 39° C., 5% $CO_2$ before transfer to recipients at GTC farm.

All experimental replicates for ATIII yielded cleavage stage embryos that were transferable on day 2 into synchronized recipients. Embryos using fibroblasts and epithelial cell phenotype as donor karyoplasts showed cleavage and development in culture. The percentage of cleavage development was higher in reconstructed couplets that used preactivated telophase II stage cytoplasts (45%) and telophase II-ethanol activated (56%) when compared to cytoplasts used at metaphase II arrested (35%) using ATIII karyoplasts. There were no differences observed in the cleavage rates of embryos that were reconstructed using donor karyoplasts in $G_0$, $G_1$ or S-phase of the cell cycle although, the morphological quality of embryos was better when donor karyoplasts were in as $G_0$ or $G_1$ compared to S-phase. Embryos were generally between the 2 to 8 cell stage with the majority of the embryos having 3–4 blastomeres at the time of transfer. Normal cleavage development corresponded chronologically to approximately 36 to 48 hours post fusion and activation. Morphologically normal appearing embryos were selected at the 2 to 8 cell stage following development in vitro for 36 to 48 hours.

Estrus Synchronization of Recipient Does

Hormonal treatments were delayed by 1 day for recipients (as compared to donor) to insure donor/recipient synchrony. Estrus was synchronized on day 1 by a 6 mg subcutaneous norgestomet ear implant. A single injection of prostaglandin was administered on day 8. Starting on day 14, a single intramuscular treatment of PMSG (CalBiochm US) was administered. The ear implant was removed on day 15. Twenty-four hours following implant removal, recipient does were mated several times to vasectomized males over three consecutive days.

Embryo Transfer to Recipient Does

Reconstructed embryos were co-cultured with GOEC monolayers for approximately 48 hours prior to transfer to synchronized recipients. Immediately prior to transfer, reconstructed embryos were placed inn equilibrated Ham's F-12 medium+10% FBS. Two to four reconstructed embryos were transferred via the fimbria into the oviductal lumen of each recipient. Transfers were performed in a minimal volume of Hams's F-12 medium+10% FBS using a sterile fire-polished glass micropipette.

The development of embryos reconstructed by nuclear transfer using transgenic caprine fetal fibroblasts and in vivo derived oocytes is summarized in Table 1. There was a total of 14 rounds of collection and transfers, with 4 donors set up for collection and 5–6 recipient does set up for transfer 48 hours later. The three different enucleation/activation protocols were employed: Metaphase II, Telophase, and Metaphase II pretreated with Ethanol. Following fusion-activation, reconstructed embryos were co-cultured with primary goat epithelial cells, at least until cleavage (2-cell stage) up to early 16-cell stage, with most embryos being transferred at chronologically correct 2- and 4-cell stages. All transfers were surgical and oviductal, in hormonally synchronized recipients (due to the season). Rates of development were slightly superior when using Telophase protocol and Ethanol protocol as compared to the Metaphase II protocol. This is partly due to the fact that enucleation of the second polar body seems less traumatic for the oocytes, and partly due to what seems to be higher activation rate for oocytes pretreated with ethanol.

TABLE 1

Development of caprine embryos reconstructed by nuclear transfer of transgenic fetal fibroblasts. Three enucleation/procedure were used; Metaphase II (first polar body enucleation), Telophase (second polar body enucleation), Ethanol (preactivation of Metaphase II stage oocytes by 7% ethanol treatment prior to enucleation). In all cases, concomitant fusion and activation was used.

| Enucleation and Activation Protocol | Oocytes Reconstructed | Oocytes Lysed (%) | Embryos Cleaved (%) | Embryos Transferred |
|---|---|---|---|---|
| Metaphase II | 138 | 67 (48.5) | 48 (35) | 47 |
| Telophase-$Ca^{2+}$ | 92 | 38 (41) | 41 (44) | 38 |
| Telophase-EtOH | 55 | 23 (42) | 31 (56) | 27 |

Following embryo transfer, recipient does were examined by ultrasound, as early as day 25. High pregnancy rates ranging from 55–78% for ATIII recipient does were diagnosed. For all three enucleation/activation protocols, it was observed that high proportion of does (65%) appeared positive at day 30. However, it must be noted that, in most cases, fetal heartbeats could not be detected at such an early stage. Moreover, the positive ultrasound signal detected at day 30 was not characteristic of normal embryo development and appeared closer to vesicular development not associated with the formation of an embryo proper. This kind of embryonic development is not typically observed in other caprine embryo transfer programs (for example with microinjected embryos). Biweekly, examination of these vesicular developments between day 25 and 40 established that these pregnancies were abnormal and at day 40, most of the fetuses were reabsorbed and normal ultrasound images were not apparent.

However, for 2 pregnancies heartbeats were detected by day 40. In these 2 cases, ultrasound examination between clay 25 and day 40, not only detected a heartbeat, but also showed the development of recognizable embryonic structures. One of these pregnancies was established using the Metaphase II enucleation/activation protocol, fusing the enucleated cytoplast to a quiescent karyoplast originating from a passage 6 culture of the CFF155-92-6 fibroblast cell line. In this instance, 4 four-cell stage reconstructed embryos were transferred to the oviduct of the recipient doe. The other pregnancy (twins) was obtained from embryos reconstructed according to the Telophase enucleation/activation protocol, fusing an enucleated cytoplast derived from preactivated telophase $Ca^{2+}$ oocytes and $G_1$ karyoplasts originating from a passage 5 culture of the CFF155-92-6 epithelial cell line. In this case, 3 reconstructed embryos (1 two-cell stage and 2 four-cell stage) were transferred to the oviduct of the recipient doe.

No pregnancies were observed with embryos generated by the Ethanol enucleation/activation protocol. However, numbers are not large enough to conclude on the relative efficacy of the 3 enucleation/activation protocols used in this study.

TABLE 2

Induction of pregnancy and further development following transfer of caprine embryos reconstructed with transgenic fetal fibroblasts and activated according to three protocols.

| Enucleation Activation Protocol | Recipients (average # of embryos/recip) | Ultrasound Results (positive/total recip) | | | Term Pregnancies |
|---|---|---|---|---|---|
| | | 30 days | 40 days | 50 days | |
| Metaphase II | 15 (3.1) | 9/15 | 1/15 | 1/15 | 1 |
| Telophase-$Ca^{2+}$ | 14 (2.7) | 11/14 | 1/14 | 1/14 | 1 (twins) |
| Telophase-EtOH | 9 (3) | 5/9 | 0/9 | 0/9 | 0 |

Perinatal Care of Recipient Embryos

Does were monitored daily throughout pregnancy for outward signs of health (e.g., appetite, alertness, appearance). Pregnancy was determined by ultrasonograph 25–28 days after the first day of standing estrus. Does were subjected to ultrasound biweekly till approximately day 75 and there after once a month to monitor the assess fetal viability. Additionally, recipient does had serum samples drawn at approximated day 21 post standing estrus for serum progesterone analysis. This was to determine if a functioning corpus luteum was present and how this compared to the animal's reproductive status (i.e., pregnancy). At approximately day 130, the pregnant does were vaccinated with tetanus toxoid and Clostridium C&D. Selenium & vitamin E (Bo-Se) and vitamins A, D, and B complex were given intramuscularly or subcutaneously and a de-wormer was administered. The does were moved to a clean kidding stall on approximately day 143 and allowed to acclimate to this new environment prior to kidding. Observations of the pregnant does were increased to monitor for signs of pending parturition. After the beginning of regular contractions, the does remained under periodic observation until birth occurred. If labor was not progressive after approximately 15 minutes of strong contractions the fetal position was assessed by vaginal palpation. If the position appeared normal then the labor was allowed to proceed for an additional 5–30 minutes (depending on the doe) before initiating an assisted vaginal birth. If indicated a cesarean section was performed. When indicated, parturition was induced with approximately 5–10 mg of PGF2α (e.g. Lutalyse). This induction can occur approximately between 145–155 days of gestation. Parturition generally occurs between 30 and 40 hours after the first injection. The monitoring process is the same as described above.

Once a kid was born, the animal was quickly towel dried and checked for gross abnormalities and normal breathing. Kids were immediately removed from the dam. Once the animal was determined to be in good health, the umbilicus was dipped in 7% tincture of iodine. Within the first hour of birth, the kids received their first feeding of heat-treated colostrum. At the time of birth, kids received injections of selenium & vitamin E (Bo-Se) and vitamins A, D, and B complex to boost performance and health.

The first transgenic female goal offspring produced by nuclear transfer was born after 154 days of gestation following the induction of parturition and cesarean delivery. The birth weight of the offspring was 2.35 kg which is with the medium weigh range of the alpine breed. The female twins were born naturally with minimal assistance a month later with a gestation length of 151 days. The birth weights of the twins were both 3.5 kg which are also within the medium weight range for twins of this breed. All three kids appeared normal and healthy and were phenotypically similar for coat color and expressing markings typical of the alpine breed. In addition, all three offspring were similar in appearance to the transgenic founder buck. No distinguishable phenotypic influence from the breed of tile donor oocyte (Saanen, Toggenburg breed) or the heterogeneous expression of the fetal genotype was observed.

Transgenic Cloned Goats

In order to confirm that the three kids were transgenic for the BC6 construct comprising the goat beta casein promoter and the human ATIII gene sequence, PR amplification and southern analysis of the segment of the transgene were performed.

Shortly after birth, blood samples and ear skin biopsies were obtained from the cloned female goats and the surrogate damns. The samples were subjected to genomic DNA isolation. Laird et al., *Nucleic Acids Res.*, 19:4293 (1991). Each sample was first analyzed by PCR using ATIII specific primers, and then subjected to Southern blot analysis using the ATIII cDNA (Edmunds et al., *Blood*, 91:4561–4571 (1998). For each sample, 5 μg of genomic DNA was digested with EcoRI (New England Biolabs, Beverly, Mass.), electrophoresed in 0.7% agarose gels (SeaKam®, Me.) and immobilized on nylon membranes (MagnaGraph, MSI, Westboro, Mass.) by capillary transfer following standard procedures (Laird et al., *Nucleic Acids Res.*, 19:4293 (1991). Membranes were probed with the 1.5 kb XhoI to SalI ATIII cDNA fragment labeled with α $^{32}$P dCTP using the Prime-It® kit (Stratagene, La Jolla, Calif.). Hybridization was executed at 65° C. overnight (Church et al., *Prot. Natl. Acad. Sci. USA*. 81:1991–1995 (1984). The blot was washed with 0.2×SSC, 0.1% SDS and exposed to X-)MAT™ AR film for 48 hours.

PCR analysis confirmed that all of the kids were transgenic for the BC6 construct comprising the goat beta cascein promoter and the human ATIII gene sequence. Southern blot analysis demonstrated the integrity of the BC6 transgene. Hybridization to a diagnostic 4.1 kb EcoRI fragment was detected for all three cloned animals, the cell lines and a transgenic positive control, but not for the two recipient does. As expected, due to cross hybridization of the ATIII cDNA probe to the endogenous goat AT locus, a 14 kb band was detected in all samples.

In addition, fluorescence in situ hybridization (FISH) was performed to determine the integration site of the BC6 construct. For typing of the cloned goats, whole blood was cultured for lymphocytes harvest (Ponce de Leon et al., *J. Hered.*, 83:36–42 (1992). Fibroblast cells and lymphocytes were pretreated and hybridized as previously described in van de Corput et al., *Histochem Cell Biol.*, 110:431–437 (1998), and Klinger et al., *Am. J. Human. Genet.*, 51:55–65 (1992). A digoxygen labeled probe containing the entire 14.7 kb BC6 transgene was used in this procedure. The TSA™ Direct system (NEN™ Life Science Products, Boston, Mass.) was used to amplify the signal. R-bands were visualized using DAPI counterstain and identified as in Di Berardino et al., *J. Hered.*, 78:225–230 (1987). A Zeiss Axioskop microscope mounted with a Hamamatsu Digital Camera was used with Image-Pro® Plus software (Media Cybernetics, Silver Spring, Md.) to capture and process images.

FISH analysis of blood cultures from each transgenic kid with probes for the BC6 transgene showed that all three carry a chromosome 5 transgene integration identical to that found in the metaphase plates derived from the CFF6 cell line. Moreover, analysis of the least 75 metaphase plates for each cloned offspring confirmed that they are not mosaic for the chromosome 5 transgenic integration.

As final confirmation that all three kids arc derived from the transgenic CFF6 cell line, PCR-RFLP analysis for the very polymorphic MHC class 11 DRB gene was undertaken. Typing for the second exon of the caprine MHC class 11 DPB gene was performed using PCR-RFLP Typing as described in Amills et al., *Immunopathol.*, 55:255–260 (1996). Fifteen microliters of nested PCR product was digested with 20 units of Rsal (New England Biolabs, Beverly, Mass.). Following digestion, restriction fragments were separated at room temperature in a 4 to 20% nondenaturing polycrylamide gel (MVP™ precast gel, Stratagene. La Jolla, Calif.) in the presence of ethidium bromide.

As illustrated by the Rsall digests of the DRB gene second exon, the three cloned offspring are identical to each other and identical to the CFF6 donor cell line, whereas the recipient does carry different alleles.

Induction of Lactation and Transgene Expression of Proteins in Milk

In order to determine whether the targeted mammary gland specific expression of human ATIII proteins were present in milk, the cloned transgenic prepubertal clones were transiently induced to lactate. At two months of age, the cloned offspring was subjected to a two week hormonal lactation-induction protocol. Hormonal induction of lactation for the CFF6-1 female was performed as described in Ryot et al., *Indian J. Anim. Res.*, 10:49–51 (1989). The CFF6-1 kid was hand-milked once daily to collect milk samples for ATIII expression analysis. All protein analysis methods were described in Edmunds et al., *Blood*, 91:4561–4571 (1998). Concentration of recombinant ATIII in the milk was determined by a rapid reverse-phase HPLC method using a Hewlett Packard 1050 HPLC (Wilmington, De.) with detection at 214 nm. The ATIII activity was evaluated by measuring thrombin inhibition with a two-stage colorimetric endpoint assay. Western blot analysis was performed with an affinity purified sheep anti-ATIII HRP conjugated polyclonal antibody (Sero Tec, Oxford, UK). Samples were boiled for 30 seconds in reducing sample buffer prior to loading onto a 10–20% gradient gel (Owl Scientific). Electrophoresis was operated at 164 volts (constant) until the dye front ran off the gel.

At the end of the treatment, small milk samples of 0.5 to 10 ml were collected daily for 20 days. The small initial volumes of milk, 0.5 to 1 ml, were typical of the amounts in prepubertal female goats hormonally induced to lactate. The volumes increased to 10 ml per day by the time the female was dried off, 25 days after the onset. The concentration and activity of ATIII in several of the samples was evaluated. As previously noted with does from this specific BC6 transgenic cell line, high levels of the recombinant ATIII was detected by Western blot analysis (Edmunds et al., *Blood*, 91:4561–4571 (1998)). The concentration of recombinant ATIII in the milk of the cloned offspring was 5.8 grams per liter (205 U/ml) at day 5, and 3.7 grams per liter (14.6 U/ml) by day 9. These were in line with levels recorded during the early part of a first natural lactation of does from this BC6 line (3.7 to 4.0 grams per liter).

Healthy transgenic goats were obtained by nuclear transfer of somatic cells to oocytes that were enucleated either in the arrested Metaphase II or the activated Telophase II -stage. These studies show that serum-starved cells used to generate term pregnancies are likely to undergo a transition following restoration with 10% serum.

Immunofloresence screening revealed that after 7 days of serum starvation fetal somatic cells were negative for $G_1$ stage cyclins D1, D2, D3 and PCNA; whereas within 3 hours of 10% FBS serum-activation a majority (e.g. approximately 70%) expressed these markers.

Reconstruction of an enucleated metaphase II arrested oocyte with the transfer of a nucleus from a donor karyoplast synchronized at $G_0$ or $G_1$ of the cell cycle following simultaneous fusion and activation mimic the chronological events occurring during fertilization. The successful development to term and birth of a normal and healthy transgenic offspring following the simultaneous fusion and activation protocol is in contrast with procedures employed in other studies that report the requirement for prolonged exposure of donor nuclei to elevated cytoplasmic MPF activity to support chromatin remodeling and reprogramming. See Campbell et al. (1996) Nature 380:64–66; Wilmut et al. (1997) Nature 385:810–813: Schnieke et al (1997) Science 278:2130–2133; Cibelli et al. (1998) Science 280:1256–1258. This result challenges the contention that prolonged remodeling of the somatic nuclei in conditions of elevated MPF activity prior to activation is important for embryonic and fetal development to term. The results also demonstrate that a reconstructed embryo may not have a requirement for prolonged exposure of tile donor nucleus to MPF nor are NEBD and PCC entirely requisite events. Rather chromatin remodeling events involving NEBD and PCC are likely permissive effects of MPF activity and, as such, may not be required for the acquisition of developmental competence or totipotency. Instead, these events are likely to serve to facilitate the acquisition of synchronicity between the cytoplast and the karyoplast. These events may even be detrimental if normal diploidy is not maintained when the donor nuclei are induced to undergo PCC with resultant chromosome dispersion due to an aberrant spindle apparatus due in part to MPF activity. Therefore, karyoplast and cytoplast synchronization with respect to cell cycle is important, first for maintenance of normal ploidy and, second for the proper induction of genome reactivation and subsequent acquisition of developmental competence of reconstructed embryos.

Further support is provided in the second method where chromatin-intact metaphase II arrested oocytes were activated to reduce MPF activity and induce the oocyte to exit the M-phase and enter the first mitotic cleavage. Approximately 3 hours post-activation, the oocytes were enucleated at telophase stage prior to the onset of $G_1$ and fused and simultaneously activated with a donor karyoplast in $G_1$ prior to START of the cycle. In addition, the simultaneous activation and fusion insured that tendencies of non-aged oocytes to revert back to an arrested state were circumvented. Using this paradigm, a normal and healthy set of twin cloned transgenic kids were produced. This procedure inherently provides a homogenous synchronization regimen for the cytoplast to coincide closer with the donor nuclei in $G_1$ prior to START. Further preactivation of the oocyte induces a decline in cytoplasmic MPF activity, thus inhibiting the occurrence of NEBD and PCC. These results suggest that NEBD and PCC is only facultative for the induction of cytoplast and karyoplast synchrony but necessary for acquisition of proper genome reactivation and subsequent development to term of the nuclear transfer embryo using somatic cell nuclei. These finding further suggest that differentiated cells at the $G_0$ or $G_1$ stage function similar to embryonic blastomeres with respect to their ability to acquire totipotency when used in combination with an arrested or an activated recipient cytoplast.

The use of both metaphase II arrested and telophase II cytoplasts provides dual options for cytoplast preparation in addition to providing an opportunity for a longer time frame to prepare the cytoplast. The use of Telophase II cytoplasts may have several practical and biological advantages. The telophase approach facilitates efficient enucleation avoiding the necessity for chromatin staining and ultraviolet localization. Moreover, enucleation at telophase enables removal of minimal cytoplasmic material and selection of a synchronous groups of activated donor cytoplasts. This procedure also allows for the preparation of highly homogenous group of donor nuclei to be synchronized with the cell cycle of the cytoplast. When used for embryo reconstruction, these populations showed a higher rate of embryonic development in vitro. Thus, reconstructed embryos comprised of a synchronously activated cytoplast and karyoplast are developmentally competent.

In addition to a successful transgenic founder production, nuclear transfer of somatic cells allows for the selection of the appropriate transgenic cell line before the generation of cloned transgenic embryos. This is particularly important in the cases where several proteins are to be co-expressed by the transgenic mammary gland. For example, the availability of several completely identical transgenic females producing recombinant human ATIII will help determine the extent of variation in the carbohydrate structure of this protein, as it is produced by the mammary gland. Thus, it may be feasible to improve the characteristics of the recombinant proteins produces in the transgenic animal system by varying environmental factors (e.g., nutrition) or to increase the milk volume yield of lactation-induction protocols to diminish further the time necessary to obtain adequate amounts of recombinant proteins for pre-clinical or clinical programs.

The high-level expression of recombinant human ATIII detected in the milk of the CFF6-1 cloned goat illustrates one of the most important aspects of this technology. By combining nuclear transfer with lactation-induction in prepubertal goats, it may be possible to characterize transgenic animals and the proteins they secrete in 8 to 9 months from the time of cell line transfection of milk expression. The amount of milk collected in an induced lactation is not only sufficient to evaluate the recombinant protein yield, but, when mg per ml expression levels are obtained, is adequate for more qualitative analysis (glycosylation, preliminary pharmacokinetics, biological and pharmacological activities). The continued availability of the transfected donor cell line also insures that genetically identical animals can be quickly generated, to rapidly supply therapeutic proteins (with predictable characteristics) for clinical trials.

EXAMPLE 3

Progression of Cytoskeletal and Nuclear Organization During in Vitro Maturation of Goat Oocytes Optimized in vitro maturation of goat oocytes is essential in efforts to characterize cell cycle dynamics throughout meiosis in the goat, and particularly in efforts to promote optimal cytoplasmic and nuclear maturation for nuclear transfer procedures. Goat oocytes were aspirated from 2–5 mm follicles from stimulated (FSH) and unstimulated (slaughterhouse) animals. Oocyte maturation was assayed by examining microtubule, microfilament and nuclear dynamics in GV (0–2–5 hrs), expected MI (12.5 hrs.), expected MII (22–23 hrs), and aged (44 hrs) oocytes, the maturation of oocytes in two different media was compared: M-199 medium (Earle's salts, 25 mM HEPES), 10% FBS, glutamine (0.1 mg/ml); M-199, 10% goat serum (from whole blood and not heat inactivated), and glutamine (0.1 mg/ml). Oocytes were simultaneously fixed and extracted suing a cytoskcletal stabilizing buffer (MTSB) for 1 hour at 37° C., and then washed and stored in block solution (PBS-Azide. 0.2%) powdered milk 2% normal goat serum, 1% BSA, 0.1 M Glycine 0.1% Triton X-100) at 4° C. prior to analysis. Oocytes were processed for immunofluorescence localization of microtubules, microfilaments and chromatin using anti-α and β tubulin monoclonal antibodies, Oregon Green phalloidin (Molecular Probes) and Hoechst 33258, respectively. Fluorescence signal was visualized using both standard immunoflourescence and confocal microscopy.

Preliminary estimates of oocytes matured in the presence of FBS show that approximately 90% progressed improperly (N=40 to date). MI spindle formation was compromised with a subsequence lack of polar body extrusion. Those oocytes which progressed to MII did so without extruding the First polar body and the MII spindle was improperly placed in the center of the cell instead of near the cortex. Preliminary estimates of oocytes matured in the presence of goat serum show that approximately 90% progressed through meiosis (N=480 to date). The morphology of the cortically placed microfilament network did not vary significantly between oocytes matured in FBS and goat serum. There may be come possible defect in polar body extrusion dynamics which is masked by the failure of the improper MI spindle morphogenesis. Further, there was no clear difference in meiotic maturation in terms of the cytoskeleton between oocytes collected from stimulated and unstimulated animals.

These data indicate that FBS is not sufficient for normal meiotic progression in vitro in the goat. Maturation media containing goat serum supports morphologically normal microtubule and spindle organization and dynamics as well as expected nuclear meiotic hallmarks. Hallmarks such as the development of the rim around the GV nucleus that is indicative of acquisition of meiotic competence as well as the condensation of DNA requisite for MI and MII progression. The goat serum which was not heat inactivated, while not selected specifically from male or female animals, must be sufficiently enriched with hormones, gonadotrophins and other factors to support mieotic progression in goat oocytes.

EXAMPLE 4

Murine Cloning

The objective of this experiment was to produce nuclear transfer embryos using activated Telophase II mouse oocytes combined with somatic cells (cumulus cells).

Oocytes were collected from superovulated mice by flushing oviducts to collect metaphase II stage oocytes. Oocytes were then activated by one of two methods to reach the Telophase II state in vitro culture-induced $Ca^{2+}$ activation or ionomycin activation (4 μM, 5 min), and enucleated. Karyoplasts were prepared from cumulus cells (natural $G_0$ stage) and nuclear transfer was conducted followed by electrical fusion with Telophase II cytoplasts.

The results of these experiments as shown in Table 2.

TABLE 2

Development of Mouse Nuclear Transfer Embryos using activated Telophase II protocol (3 replicate experiments)

| Protocol | Number | Percent |
|---|---|---|
| Oocytes Recovered | 202 | |
| Activation: | 47/52 | 90 |
| Culture induced $Ca^{2+}$ | | |
| Activation: | 46/50 | 92 |
| Ionomycin indiced $Ca^{2+}$ | | |
| Oocytes Enucleated & Reconstructed | 85 | 42 |
| Embryo cleavage (2-cell) | 51 | 60 |
| Transferred embryos | 21 | 41 |
| Recipients | 3 | Na |
| Pregnancy (day 11–15) | 2/3 | 66 |
| Term Pregnancy | 1 | 33 |
| (ceasarian day 20) | | |
| Offspring (total) | 3 (stillborn) | na |
| Offspring (% of total transferred) | 3/21 | 14.3 |

EXAMPLE 5

In Vitro Maturation of Transported Pig Oocytes in a Defined Protein-free Medium

Improved efficiency of in vitro embryo production of embryo cloning using nuclear transfer, will rely on a detailed understanding of cellular and nuclear progression during in vitro oocyte maturation (IVM) in pigs. The objective of this study was to demonstrate precisely the progression of chromatin and microtubule dynamics in pig oocytes during IVM using a defined protein-free medium. Follicles from abattoir ovaries were aspirated with 18 G-needles. Cumulus-oocyte-complexes (COCs) were washed and cultured in 0.5 mL tubes in pre-equilibrated (5% $CO_2$) M199 medium containing polyvinyl alcohol (0.1%) cystein (0.1 mg/mL), EGF (10 ng/mL), Pen/Strep, hCG (10 IUmL) and PMSG (10 IU/mL; Abeydeera et al. *Biol. Reprod.* 58:1316–1320 (1998). Oocytes were then transported (Minitube incubator, 39° C.) over night by air-courier. Upon receipt (24 h of maturation COGs were freed of cumulus and corona cells and fixed in microtubule stabilization buffer (1 h, 37° C.). Fixed oocytes were stored (PBS, 0.1% PVA) at 4° C. prior to staining. Fluorescence staining for microtubules and chromatin was preformed. Stained oocytes were mounted on slides (PBS/ 50% glycerine) and evaluated at ×400 magnification (see Table 3).

TABLE 3

Developmental stages of pig oocytes at different time-points of in vitro maturation

| Time of Maturation (h post aspiration) | N | Germinal Vesicle GV (%) | germinal vesicle breakdown GVBD (%) | MI (%) | anaphase/telophase (%) | MII (%) | degenerated or spontaneously activated (%) |
|---|---|---|---|---|---|---|---|
| 26 h | 53 | 16 (30.2) | 23 (43.4) | 11 (20.8) | 1 (1.9) | 0 | 2 (3.8) |
| 29 h | 51 | 18 (35.3) | 12 (23.5) | 17 (33.3) | 1 (2.0) | 1 (2.0) | 2 (3.9) |

TABLE 3-continued

Developmental stages of pig oocytes at different time-points of in vitro maturation

| Time of Maturation (h post aspiration) | N | Germinal Vesicle GV (%) | germinal vesicle breakdown GVBD (%) | MI (%) | anaphase/telophase (%) | MII (%) | degenerated or spontaneously activated (%) |
|---|---|---|---|---|---|---|---|
| 32 h | 53 | 5 (9.4) | 10 (18.9) | 27 (50.9) | 3 (5.7) | 2 (3.8) | 6 (11.3) |
| 35 h | 52 | 3 (5.8) | 7 (13.5) | 29 (55.8) | 6 (11.5) | 5 (9.6) | 2 (3.8) |
| 38 h | 54 | 6 (11.1) | 3 (5.6) | 25 (46.3) | 5 (9.3) | 14 (25.9) | 1 (1.9) |
| 41 h | 51 | 4 (7.8) | 6 (11.8) | 8 (15.7) | 2 (3.9) | 27 (52.9) | 4 (7.8) |
| 44 h | 99 | 10 (10.1) | 4 (4.0) | 8 (8.1) | 0 | 76 (76.8) | 1 (1.0) |

Progressive changes in chromatin and microtubular configuration, from asters that associated to the chromatin during prometaphase, to further chromatin condensation and elongation of the meiotic spindle until Telophase I, and followed by the extrusion of the first polar body were observed and photodocumented. In conclusion, the percentage of MII-oocytes at 44 h of maturation (76%) is comparable to the results after routine IVM using the same protocol (86% Abeydeera et al., 1998). Our data indicate, that the defined, protein-free medium effectively supports IVM of procine oocytes, subjected to overnight transport during the first 24 h of IVM.

EXAMPLE 6

Differential Expression of E-cadherin and Na+/K+ ATPase Proteins in Parthenogenetic Pig Embryos Parthenogenetic activation of porcine oocytes supports limited and variable embryonic development in vitro and in silo. As parthenotes develop devoid of parental genes, the objective of the study was to assess the ability of the maternal genome to direct the key developmental processes of embryo compaction and cavitation. Expression and localization of E-cadherin, an important transmembrane cell adhesion molecule involved in compaction, and Na+/K= ATPase, an active transmembrane ion transporting enzyme involved in cavitation, were characterized in both in vivo produced embryos and parthenogenetic pig embryos that development in vitro following activation. Pig ovaries were obtained from slaughter house material and oocytes were aspirated (2.6 mm follicles), washed in Hepes-buffered Tyrode's solution (HbT) and matured in Waymouth MB medium containing 10 IU hCG, 10% fetal bovine serum and 10% (v/v) porcine follicular fluid for 20 h, followed by an additional 24 h without hormones. Oocytes were activated by electrical pulse (5 V AC followed by 1.44kV/cm DC for 31.2 msec) in Hbt-0.3 M mannitol in 5% HbT, and transferred surgically into ligated oviducts of synchronous recipient gilts. Parthenogenetic and in vivo produced (natural cycle) embryos were recovered at cleavage or morula stages of development on days 3 or 6 following transfer. Embryos were washed (2×HbT) and fixed in either microtubule stabilizing buffer (MTSB; 0.1 M PIPES, 5 mM $MgCl_2$, 2.5 mM EGTA, 0.01% aprotinin, 1 mM DTT, 50% deuterium oxide, 1 μM Taxol®, 0.1% Triton X-100, 3.7% formalin) or 4% paraformaldehyde/0.5% saponin for 60 minutes at 37° C. Individual embryos were processed for immunofluorescence localization of E-cadherin (anti-E-cadherin MAB/GAR-Cy3, 23° C., 2 hr) or Na+/K+ ATPase (anti-α/β subunit MAB/GAR-Cy3, 23° C. 2 h), followed by staining of nuclei (Hoechst 33258, 10 μg/ml in PBS, 37° C. 15 min.). Single embryos were mounted on glass slides (50% glycerol in PBS) and subsequently analyzed using conventional and confocal fluorescence microscopy. Na+/K+ ATPase staining was first apparent at abutting blastomere cell borders of compacted morulae in both in vivo and parthenogenetic embryos. Similarly, Na+ pump subunits were uniformly localized at the basal lateral domains of trophectoderm cells of both in vivo and parthenogenetic blastocysts. E-cadherin was localized to cortical regions of cell-cell contact in most blastomeres of 8-cell embryos and uncompacted and compacted morulae and in trophectodermal cells of blastocysts produced in vivo. In contrast, E-cadherin was observed as heterogeneous cortical staining among blastomeres of parthenogenetic embryos at all embryonic stages. Further, parthenogenetic embryos of poor morphological quality displayed extensive disruption of cortical E-cadherin staining. These results suggest that expression of E-cadherin (compaction) but not Na+/K+ ATPase (cavitation) may require paternal genome participation for normal blastomere differentiation prior to compaction since differential expression of these proteins coincides temporally with the time of zygotic gene activation in the pig. Alternatively, the observed heterogeneous protein/gene expression and cellular localization patterns may be a result of aberrant chromosomal segregation.

The teachings of all the patents, patent applications and publications cited herein are incorporated by reference in their entirety.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of cloning a mammal, comprising the steps of:

a. fusing a somatic activated donor cell and an activated, enucleated oocyte in telophase II and of the same species as the donor cell, to thereby form a nuclear transfer embryo;

b. impregnating a mammal of the same species as the nuclear transfer embryo with the fused nuclear transfer embryo under conditions suitable for gestation of the cloned mammal; and c. gestating the embryo in step b., thereby causing the embryo to develop into the cloned mammal.

2. The method of claim 1, wherein the activated donor cell is in the $G_1$ stage of a mitotic cell cycle.

3. The method of claim 2, wherein the somatic cell is an adult somatic cell or an embryonic somatic cell.

4. The method of claim 2, wherein the somatic cell is a fibroblast cell or an epithelial cell.

5. The method of claim 1, wherein the oocyte is enucleated chemically, by X-ray irradiation, by laser irradiation or by physical removal.

6. A method of producing a transgenic mammal, comprising the steps of:

a. fusing a somatic activated donor cell having a genetically engineered nucleus and an activated, enucleated oocyte in telophase II and of the same species as the donor cell, to thereby form a transgenic nuclear transfer embryo;

b. impregnating a mammal of the same species as the nuclear transfer embryo with the fused, nuclear transfer embryo under conditions suitable for gestation of the transgenic mammal; and c. gestating the embryo in step b., thereby causing the embryo to develop into the transgenic mammal.

7. The method of claim 6, wherein the activated donor cell is in the $G_1$ stage of a mitotic cell cycle.

8. A method of producing a mammalian nuclear transfer embryo, comprising fusing a somatic activated donor cell and an activated, enucleated oocyte in telophase II and of the same species as the donor cell, to thereby form a nuclear transfer embryo.

9. The method of claim 8, wherein the oocyte is activated by exposing the oocyte to increased levels of calcium.

10. The method of claim 9, further including decreasing phosphorylation in the oocyte.

11. The method of claim 10, wherein the oocyte is activated by subjecting the oocyte to ethanol, ionophore or electrical stimulation in the presence of calcium.

12. The method of claim 8, wherein the oocyte is in metaphase II prior to activation to telophase II.

13. The method of claim 8, wherein the somatic donor cell is activated by reducing nutrients in the serum of the donor cell, and then exposing the donor cell to serum having an increased amount of nutrients.

14. The method of claim 13, wherein the somatic activated donor cell is in the $G_1$ stage of a mitotic cell cycle.

15. A method of cloning a mammalian fetus, comprising the steps of:
   a. fusing a somatic activated donor cell and an activated, enucleated oocyte in telophase II and of the same species as the donor cell, to thereby form a nuclear transfer embryo;
   b. impregnating a mammal of the same species as the nuclear transfer embryo with the fused nuclear transfer embryo under conditions suitable for gestation of the cloned mammalian fetus; and
   c. gestating the embryo in step b., thereby causing the embryo to develop into the cloned mammalian fetus.

16. The method of claim 15, wherein the activated donor cell is in the $G_1$ stage of a mitotic cell cycle.

17. The method of claim 15, wherein the somatic cell is an adult somatic cell or an embryonic somatic cell.

18. The method of claim 15, wherein the somatic cell is a fibroblast cell or an epithelial cell.

19. The method of claim 15, wherein the oocyte is enucleated chemically, by X-ray irradiation, by laser irradiation or by physical removal.

20. A method of cloning a non-human mammal, comprising the steps of:
   a. fusing a somatic activated donor cell and an activated, enucleated oocyte in telophase II and of the same species as the donor cell, to thereby form a nuclear transfer embryo;
   b. impregnating a non-human mammal of the same species as the nuclear transfer embryo with the fused nuclear transfer embryo under conditions suitable for gestation of the cloned non-human mammal; and
   c. gestating the embryo in step b., thereby causing the embryo to develop into the cloned non-human mammal.

21. The method of claim 20, wherein the activated donor cell is in the $G_1$ stage of a mitotic cell cycle.

22. The method of claim 20, wherein the somatic cell is an adult somatic cell or an embryonic somatic cell.

23. The method of claim 20, wherein the somatic cell is a fibroblast cell or an epithelial cell.

24. The method of claim 20, wherein the oocyte is enucleated chemically, by X-ray irradiation, by laser irradiation or by physical removal.

25. A method of producing a transgenic non-human mammal, comprising the steps of:
   a. fusing a somatic activated donor cell having a genetically engineered nucleus and an activated, enucleated oocyte in telophase II and of the same species as the donor cell, to thereby form a transgenic nuclear transfer embryo;
   b. impregnating a non-human mammal of the same species as the nuclear transfer embryo with the transgenic nuclear transfer embryo under conditions suitable for gestation of the transgenic non-human mammal; and
   c. gestating the embryo in step b., thereby causing the embryo to develop into the transgenic non-human mammal.

26. The method of claim 25, wherein the activated donor cell is in the $G_1$ stage of a mitotic cell cycle.

27. The method of claim 25, wherein the somatic cell is an adult somatic cell or an embryonic somatic cell.

28. The method of claim 25, wherein the somatic cell is a fibroblast cell or an epithelial cell.

29. The method of claim 25, wherein the oocyte is enucleated chemically, by X-ray irradiation, by laser irradiation or by physical removal.

30. A method of cloning a non-human mammalian fetus, comprising the steps of:
   a. fusing a somatic activated donor cell and an activated, enucleated oocyte in telophase II and of the same species as the donor cell, to thereby form a nuclear transfer embryo;
   b. impregnating a non-human mammal of the same species as the nuclear transfer embryo with the fused nuclear transfer embryo under conditions suitable for gestation of the cloned non-human mammalian fetus; and
   c. gestating the embryo in step b., thereby causing the embryo to develop into the non-human mammalian fetus.

31. The method of claim 30, wherein the activated donor cell is in the $G_1$ stage of a mitotic cell cycle.

32. The method of claim 30, wherein the somatic cell is an adult somatic cell or an embryonic somatic cell.

33. The method of claim 30, wherein the somatic cell is a fibroblast cell or an epithelial cell.

34. The method of claim 30, wherein the oocyte is enucleated chemically, by X-ray irradiation, by laser irradiation or by physical removal.

35. A method of cloning a mammal, comprising the steps of:
   a. fusing a somatic activated donor cell and an activated, enucleated oocyte derived from an oocyte having a first polar body and an extruding second polar body, and of the same species as the donor cell, to thereby form a nuclear transfer embryo;
   b. impregnating a mammal of the same species as the nuclear transfer embryo with the fused nuclear transfer embryo under conditions suitable for gestation of the cloned mammal; and
   c. gestating the embryo in step b., thereby causing the embryo to develop into the cloned mammal.

36. The method of claim 35, wherein the activated donor cell is in the $G_1$ stage of a mitotic cell cycle.

37. The method of claim 35, wherein the somatic cell is an adult somatic cell or an embryonic somatic cell.

38. The method of claim 35, wherein the somatic cell is a fibroblast cell or an epithelial cell.

39. The method of claim 35, wherein the oocyte is enucleated chemically, by X-ray irradiation, by laser irradiation or by physical removal.

40. A method of producing a transgenic mammal, comprising the steps of:
   a. fusing a somatic activated donor cell having a genetically engineered nucleus and an activated, enucleated oocyte derived from an oocyte having a first polar body and an extruding second polar body, and of the same species as the donor cell, to thereby form a transgenic nuclear transfer embryo;
   b. impregnating a mammal of the same species as the nuclear transfer embryo with the fused transgenic nuclear transfer embryo under conditions suitable for gestation of the transgenic mammal; and
   c. gestating the embryo in step b., thereby causing the embryo to develop into the transgenic mammal.

41. The method of claim 40, wherein the activated donor cell is in the $G_1$ stage of a mitotic cell cycle.

42. The method of claim 40, wherein the somatic cell is an adult somatic cell or an embryonic somatic cell.

43. The method of claim 40, wherein the somatic cell is a fibroblast cell or an epithelial cell.

44. The method of claim 40, wherein the oocyte is enucleated chemically, by X-ray irradiation, by laser irradiation or by physical removal.

45. A method or producing a nuclear transfer embryo, comprising combining a nucleus from a somatic activated donor cell with an activated, enucleated oocyte derived from an oocyte having a first polar body and an extruding second polar body, and of the same species as the donor cell, to thereby form a nuclear transfer embryo.

46. A method of producing a mammalian fetus, comprising the steps of:
   a. fusing a somatic activated donor cell and an activated, enucleated oocyte derived from an oocyte having a first polar body and an extruding second polar body, and of the same species as the donor cell, to thereby form a nuclear transfer embryo;
   b. impregnating a mammal of the same species as the nuclear transfer embryo with the fused nuclear transfer embryo under conditions suitable for gestation of the mammalian fetus; and
   c. gestating the embryo in step b., thereby causing the embryo to develop into the mammalian fetus.

47. The method of claim 46, wherein the activated donor cell is in the $G_1$ stage of a mitotic cell cycle.

48. The method of claim 46, wherein the somatic cell is an adult somatic cell or an embryonic somatic cell.

49. The method of claim 46, wherein the somatic cell is a fibroblast cell or an epithelial cell.

50. The method of claim 46, wherein the oocyte is enucleated chemically, by X-ray irradiation, by laser irradiation or by physical removal.

51. A method of cloning a mammal, comprising the steps of:
   a. injecting contents of a somatic activated donor cell including a nucleus into an activated, enucleated oocyte in telophase H and of the same species as the donor cell, to thereby form a nuclear transfer embryo;
   b. impregnating a mammal of the same species as the nuclear transfer embryo with the fused nuclear transfer embryo under conditions suitable for gestation of the cloned mammal; and
   c. gestating the embryo in step b., thereby causing the embryo to develop into the cloned mammal.

52. A method of producing a transgenic mammal, comprising the steps of:
   a. injecting contents of a somatic activated donor cell including a genetically engineered nucleus into an activated, enucleated oocyte in telophase II and of the same species as the donor cell, to thereby form a transgenic nuclear transfer embryo;
   b. impregnating a mammal of the same species as the nuclear transfer embryo with the fused, nuclear transfer embryo under conditions suitable for gestation of the transgenic mammal; and
   c. gestating the embryo in step b., thereby causing the embryo to develop into the transgenic mammal.

53. A method of producing a mammalian nuclear transfer embryo, comprising injecting contents of a somatic activated donor cell including a nucleus with an activated, enucleated oocyte in telophase II and of the same species as the donor cell, to thereby form a nuclear transfer embryo.

54. A method of cloning a mammalian fetus, comprising the steps of:
   a. injecting contents of a somatic activated donor cell including a nucleus into an activated, enucleated oocyte in telophase II and of the same species as the donor cell, to thereby form a nuclear transfer embryo;
   b. impregnating a mammal of the same species as the nuclear transfer embryo with the fused nuclear transfer embryo under conditions suitable for gestation of the cloned mammalian fetus; and
   c. gestating the embryo in step b., thereby causing the embryo to develop into the cloned mammalian fetus.

55. A method of cloning a non-human mammal, comprising the steps of:
   a. injecting contents of a somatic activated donor cell including a nucleus into an activated, enucleated oocyte in telophase II and of the same species as the donor cell, to thereby form a nuclear transfer embryo;
   b. impregnating a non-human mammal of the same species as the nuclear transfer embryo with the fused nuclear transfer embryo under conditions suitable for gestation of the cloned non-human mammal; and
   c. gestating the embryo in step b., thereby causing the embryo to develop into the cloned non-human mammal.

56. A method of producing a transgenic non-human mammal, comprising the steps of:
   a. injecting contents of a somatic activated donor cell including a genetically engineered nucleus into an activated, enucleated oocyte in telophase II and of the same species as the donor cell, to thereby form a transgenic nuclear transfer embryo;
   b. impregnating a non-human mammal of the same species as the nuclear transfer embryo with the transgenic nuclear transfer embryo under conditions suitable for gestation of the transgenic non-human mammal; and
   c. gestating the embryo in step b., thereby causing the embryo to develop into the transgenic non-human mammal.

57. A method of cloning a non-human mammalian fetus, comprising the steps of:
   a. injecting contents of a somatic activated donor cell including a nucleus into an activated, enucleated oocyte in telophase II and of the same species as the donor cell, to thereby form a nuclear transfer embryo;
   b. impregnating a non-human mammal of the same species as the nuclear transfer embryo with the fused nuclear transfer embryo under conditions suitable for gestation of the cloned non-human mammalian fetus; and
   c. gestating the embryo in step b., thereby causing the embryo to develop into the cloned non-human mammalian fetus.

58. A method of cloning a mammal, comprising the steps of:
   a. injecting contents of a somatic activated donor cell including a nucleus into an activated, enucleated oocyte derived from an oocyte having a first polar body and an extruding second polar body, and of the same species as the donor cell, to thereby form a nuclear transfer embryo;
   b. impregnating a mammal of the same species as the nuclear transfer embryo with the fused nuclear transfer embryo under conditions suitable for gestation of the cloned mammal; and
   c. gestating the embryo in step b., thereby causing the embryo to develop into the cloned mammal.

59. A method of producing a transgenic mammal, comprising the steps of:

a. injecting contents of a somatic activated donor cell including a genetically engineered nucleus into an activated, enucleated oocyte derived from an oocyte having a first polar body and an extruding second polar body, and of the same species as the donor cell, to thereby form a transgenic nuclear transfer embryo;

b. impregnating a mammal of the same species as the nuclear transfer embryo with the fused transgenic nuclear transfer embryo under conditions suitable for gestation of the transgenic mammal; and c. gestating the embryo in step b., thereby causing the embryo to develop into the transgenic mammal.

60. A method of producing a mammalian fetus, comprising the steps of:

a. injecting contents of a somatic activated donor cell including a nucleus into an activated, enucleated oocyte derived from an oocyte having a first polar body and an extruding second polar body, and of the same species as the donor cell, to thereby form a nuclear transfer embryo;

b. impregnating a mammal of the same species as the nuclear transfer embryo with the fused nuclear transfer embryo under conditions suitable for gestation of the cloned fetus; and c. gestating the embryo in step b., thereby causing the embryo to develop into the mammalian fetus.

* * * * *

SEQUENCE LISTING

<160> NUMBER OF SEQ ID NOS: 4

<210> SEQ ID NO 1
<211> LENGTH: 28

```
<212> TYPE: DNA
<213> ORGANISM: Artificial Sequence
<220> FEATURE:
<223> OTHER INFORMATION: Primer

<400> SEQUENCE: 1
ctccatcagt tgctggaggg tgtcatta                                          28

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
gaaggtttat cttttgtcct tgctgctca                                         29

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ataatcacat ggagagccac aagc                                              24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
gcacttcttt ggtatctgag aaag                                              24
```